US012616475B2

(12) United States Patent
Nicholas

(10) Patent No.: US 12,616,475 B2
(45) Date of Patent: May 5, 2026

(54) POWERED SURGICAL STAPLING DEVICE WITH END EFFECTOR ARTICULATION

(71) Applicant: Covidien LP, Mansfield, MA (US)

(72) Inventor: David A. Nicholas, North Haven, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/994,272

(22) PCT Filed: Jul. 24, 2023

(86) PCT No.: PCT/IB2023/057501

§ 371 (c)(1),
(2) Date: Jan. 14, 2025

(87) PCT Pub. No.: WO2024/023682

PCT Pub. Date: Feb. 1, 2024

(65) Prior Publication Data

US 2026/0026812 A1     Jan. 29, 2026

Related U.S. Application Data

(60) Provisional application No. 63/391,932, filed on Jul. 25, 2022.

(51) Int. Cl.
*A61B 17/072*     (2006.01)
*A61B 17/00*     (2006.01)
*A61B 17/29*     (2006.01)

(52) U.S. Cl.
CPC ................... *A61B 17/07207* (2013.01); *A61B 2017/00398* (2013.01); *A61B 2017/0046* (2013.01); *A61B 2017/07257* (2013.01); *A61B*
*2017/07271* (2013.01); *A61B 2017/2913* (2013.01); *A61B 2017/2923* (2013.01); *A61B 2017/2927* (2013.01)

(58) Field of Classification Search
CPC ................................................. A61B 17/07207
See application file for complete search history.

(56) References Cited

U.S. PATENT DOCUMENTS 7,963,433 B2     6/2011   Whitman et al.
8,322,455 B2     12/2012   Shelton, IV et al.
(Continued)

FOREIGN PATENT DOCUMENTS

CN         107811666         3/2018
EP         3476329         5/2019

OTHER PUBLICATIONS

PCT/IB2023/057501, The International Search Report and Written Opinion, mailed Nov. 30, 2023, 15pgs.

*Primary Examiner* — Nathaniel C Chukwurah

(57) ABSTRACT

A powered stapling device includes an adapter assembly that includes an outer tube, a shifter mechanism, an articulation gear, and a rotate gear. The rotate gear is secured to the outer tube such that rotation of the rotate gear causes rotation of the outer tube. The shifter mechanism includes a shifter shaft that supports a shifter gear. The shifter shaft is movable to move the shifter gear between a rotate position in which rotation of the articulation gear causes rotation of the rotate gear and the outer tube and an articulate position in which the shifter gear prevents or locks rotation of the rotate gear and the outer tube.

20 Claims, 18 Drawing Sheets

(56) References Cited

U.S. PATENT DOCUMENTS

| | | | | |
|---|---|---|---|---|
| 8,573,465 | B2 | 11/2013 | Shelton, IV | |
| 9,993,258 | B2 | 6/2018 | Shelton, IV et al. | |
| 10,702,266 | B2 | 7/2020 | Parihar et al. | |
| 11,013,563 | B2 | 5/2021 | Shelton, IV et al. | |
| 11,141,156 | B2 | 10/2021 | Shelton, IV | |
| 11,241,228 | B2 | 2/2022 | Nicholas et al. | |
| 11,259,801 | B2 * | 3/2022 | Zemlok et al. | |
| 2008/0255418 | A1 * | 10/2008 | Zemlok ................ | A61B 17/072 |
| | | | | 600/118 |
| 2009/0108048 | A1 * | 4/2009 | Zemlok .................. | G16Z 99/00 |
| | | | | 227/176.1 |
| 2012/0292367 | A1 | 11/2012 | Morgan et al. | |
| 2016/0302790 | A1 | 10/2016 | Williams et al. | |
| 2017/0281189 | A1 | 10/2017 | Nalagatla et al. | |

\* cited by examiner

POWERED SURGICAL STAPLING DEVICE WITH END EFFECTOR ARTICULATION

CROSS-REFERENCE TO RELATED APPLICATIONS

This application is a National Stage Application of PCT/IB2023/057501 filed Jul. 24, 2023, which claims benefit of and priority to U.S. Provisional Application No. 63/391,932 filed Jul. 25, 2022, and the disclosures of each of the above-identified applications are hereby incorporated by reference in their entirety.

FIELD

The disclosure relates generally to surgical devices for endoscopic use and, more specifically, to powered surgical stapling devices for endoscopic use with powered end effector articulation and rotation.

BACKGROUND

Various types of surgical devices used to endoscopically treat tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical device is a surgical stapling device. Typically, surgical stapling devices include a handle assembly, an adapter assembly that is coupled to the handle assembly, and an end effector that is supported on a distal end of the adapter assembly. The end effector includes an anvil assembly and a cartridge assembly for supporting an array of surgical staples. The end effector and/or the adapter assembly includes an approximation mechanism for moving the cartridge and anvil assemblies between open and clamped positions, and a firing mechanism for ejecting the surgical staples from the cartridge assembly.

During laparoscopic or endoscopic surgical procedures, access to a surgical site is achieved through a small incision or through a narrow cannula inserted through a small entrance wound in a patient. Because of limited area available to access the surgical site, many endoscopic devices include mechanisms for rotating the adapter assembly and end effector in relation to the handle assembly, and for articulating the end effector of the device in relation to the adapter assembly of the device to improve access to tissue to be treated.

Surgical stapling devices can be manually driven or powered. Typically, powered stapling devices include one or more motors in the handle assembly to power one or more of the functional operations of the device, e.g., approximation, firing, articulation, and rotation. Most powered devices include stationary motors in the handle assembly to power articulation. Since the adapter assembly is adapted for rotation in relation to the handle assembly and the motor for providing end effector articulation is stationary within the handle assembly, most powered stapling device designs require decoupling of the rotary motor output within the handle assembly from the linear moving shaft components within the adapter assembly to accomplish articulation and/or rotation of the end effector. These designs can be complex and/or expensive.

A continuing need exists for a reliable, less complex, powered surgical stapling device with rotation and articulation capabilities.

SUMMARY

This disclosure is directed to a powered stapling device that includes an adapter assembly having an outer tube, a shifter mechanism, an articulation gear, and a rotate gear. The rotate gear is secured to the outer tube such that rotation of the rotate gear causes rotation of the outer tube. The shifter mechanism includes a shifter shaft that supports a shifter gear. The shifter shaft is movable to move the shifter gear between a rotate position in which rotation of the articulation gear causes rotation of the rotate gear and the outer tube and an articulate position in which the shifter gear prevents rotation of the rotate gear and the outer tube.

Aspects of the disclosure are directed to a powered surgical device including a handle assembly and an adapter assembly. The adapter assembly defines a longitudinal axis and includes a coupling assembly, a drive assembly, a drive shaft, an outer tube, and an articulation mechanism. The coupling assembly has a body defining a central through bore, a second bore, and a third bore. The body is non-rotatably coupled to the handle assembly. The drive assembly is received within the central through bore and includes a drive screw and a drive member threadedly coupled to the drive screw. The drive member is longitudinally movable along the drive screw in response to rotation of the drive screw. The drive shaft supports a drive gear and is positioned within the second bore. The outer tube has a proximal portion and a distal portion and is rotatable in relation to the coupling assembly. The articulation mechanism is positioned within the outer tube and includes an articulation gear, a barrel cam, a first link extension, a second link extension, a rotate gear, and a shifter mechanism. The articulation gear is engaged with the drive gear and is rotatable in response to rotation of the drive gear. The barrel cam is fixedly supported within the articulation gear and defines first and second cam channels. The first link extension has a proximal portion and a distal portion. The proximal portion supports a first cam member that is received in the first cam channel. The second link extension has a proximal portion and a distal portion. The proximal portion of the second link extension supports a second cam member that is received in the second cam channel. The rotate gear is coupled to the outer tube and is rotatable in relation to the body of the coupling assembly to rotate the outer tube in relation to the coupling assembly. The shifter mechanism is received within the third bore of the body of the coupling assembly and includes a shifter shaft and a shifter gear that is secured to the shifter shaft. The shifter shaft is movable between a rotate position in which the shifter gear is coupled with the articulation gear and the rotate gear and an articulate position in which the shifter gear is engaged with the rotate gear and disengaged from the articulation gear.

Other aspects of the disclosure are directed to an adapter assembly including a coupling assembly, a rotation member, a drive assembly, a drive shaft, an outer tube, an articulation mechanism, a rotate gear, and a shifter mechanism. The coupling assembly has a body defining a central through bore, a second bore, and a third bore. The body is non-rotatably coupled to the handle assembly. The rotation member is rotatably supported in relation to the body of the coupling assembly. The drive assembly is received within the central through bore and includes a drive screw and a drive member threadedly coupled to the drive screw. The drive member is longitudinally movable along the drive screw in response to rotation of the drive screw. The drive shaft supports a drive gear, and the drive shaft is positioned within the second bore. The outer tube has a proximal portion and a distal portion. The outer tube is secured to the rotation member and is rotatable in relation to the coupling assembly. The articulation mechanism is positioned within the outer tube and includes an articulation gear, a barrel cam, a first link extension, and a second link extension. The articulation gear is engaged with the drive gear and is rotatable in response to rotation of the drive gear. The barrel cam is fixedly supported within the articulation gear and defines first and second cam channels. The first link extension has a proximal portion and a distal portion. The proximal portion supports a first cam member that is received in the first cam channel. The second link extension has a proximal portion and a distal portion. The proximal portion of the second link extension supports a second cam member that is received in the second cam channel. The rotate gear is coupled to the outer tube and is rotatable in relation to the body of the coupling assembly to rotate the outer tube and the rotation member in relation to the coupling assembly. The shifter mechanism is received within the third bore of the body of the coupling assembly and includes a shifter shaft and a shifter gear that is secured to the shifter shaft. The shifter shaft is movable between a rotate position in which the shifter gear is coupled with the articulation gear and the rotate gear and an articulate position in which the shifter gear is engaged with the rotate gear and disengaged from the articulation gear.

Still other aspects of the disclosure are directed to a powered surgical device including a handle assembly, an adapter assembly, and an end effector. The adapter assembly defines a longitudinal axis and includes a coupling assembly, a rotation member, a drive assembly, a drive shaft, an outer tube, an articulation mechanism, a rotate gear, and a shifter mechanism. The coupling assembly has a body defining a central through bore, a second bore, and a third bore. The body is non-rotatably coupled to the handle assembly. The drive assembly is received within the central through bore and includes a drive screw and a drive member threadedly coupled to the drive screw. The drive member is longitudinally movable along the drive screw in response to rotation of the drive screw. The drive shaft supports a drive gear and is positioned within the second bore of the body of the coupling assembly. The outer tube has a proximal portion and a distal portion and is rotatable in relation to the coupling assembly. The articulation mechanism is positioned within the outer tube and includes an articulation gear, a barrel cam, a first link extension, and a second link extension. The articulation gear is engaged with the drive gear and is rotatable in response to rotation of the drive gear. The barrel cam is fixedly supported within the articulation gear and defines first and second cam channels. The first link extension has a proximal portion and a distal portion. The proximal portion supports a first cam member that is received in the first cam channel. The second link extension has a proximal portion and a distal portion. The proximal portion of the second link extension supports a second cam member that is received in the second cam channel. The rotate gear is coupled to the outer tube and is rotatable in relation to the body of the coupling assembly to rotate the outer tube in relation to the coupling assembly. The shifter mechanism is received within the third bore of the body of the coupling assembly and includes a shifter shaft and a shifter gear that is secured to the shifter shaft. The shifter shaft is movable between a rotate position in which the shifter gear is coupled with the articulation gear and the rotate gear and an articulate position in which the shifter gear is engaged with the rotate gear and disengaged from the articulation gear. The end effector is secured to the distal portion of the adapter assembly about an articulation axis that is transverse to the longitudinal axis and includes an anvil assembly and a cartridge assembly. The first and second link extensions are coupled to the end effector and are movable to articulate the end effector about the articulation axis.

In aspects of the disclosure, the body of the coupling assembly of the adapter assembly defines a splined opening, and the shifter gear is received within the splined opening when the shifter shaft is in the articulate position to prevent rotation of the outer tube in relation to the body of the coupling assembly.

In some aspects of the disclosure, the shifter mechanism includes an articulate pinion that is rotatably supported on the shifter shaft, and the articulate piston defines a splined bore.

In certain aspects of the disclosure, the shifter gear has a splined extension that is received within the splined bore of the articulate piston to rotatably secure the shifter gear to the articulate piston.

In aspects of the disclosure, the adapter assembly includes a biasing member that is positioned to urge the splined extension into the splined bore to couple the shifter gear to the articulate piston.

In some aspects of the disclosure, the shifter mechanism includes a splined collar that is secured within the body of the coupling assembly and defines the splined opening.

In certain aspects of the disclosure, the splined collar includes wings, and the body of the coupling assembly defines slots that receive the wings to prevent rotation of the splined collar in relation to the body of the coupling assembly.

In aspects of the disclosure, the powered surgical device includes an end effector supported on the distal portion of the outer tube.

In some aspects of the disclosure, the end effector includes an anvil assembly and a cartridge assembly, and the end effector is movable between open and clamped positions.

In certain aspects of the disclosure, the end effector is secured to the distal portion of the outer tube about an articulation axis that is transverse to the longitudinal axis defined by the adapter assembly.

In aspects of the disclosure, the first and second link extensions are coupled to the end effector and movable to articulate the end effector about the articulation axis.

In some aspects of the disclosure, the articulation mechanism further includes first and second articulation links, and the first articulation link couples the first link extension to the end effector and the second articulation link couples the second link extension to the end effector.

In certain aspects of the disclosure, the adapter assembly further includes a rotation member that is supported about the proximal portion of the outer tube.

In aspects of the disclosure, the rotation member is secured to the outer tube by an attachment ring.

In some aspects of the disclosure, the attachment ring includes an annular base and resilient fingers that extend from the annular base and have inwardly extending tabs, and the outer tube defines spaced openings that receive the tabs.

In certain aspects of the disclosure, each of the first and second cam members includes a rectangular body portion, a post, and a follower, and the followers are received within the first and second cam channels.

In aspects of the disclosure, that outer tube defines elongate slots, and each of the posts extend through one of the elongate slots such that the first and second link extensions are supported within the outer tube and the followers are positioned on an outer surface of the outer tube.

Other features of the disclosure will be appreciated from the following description.

BRIEF DESCRIPTION OF THE DRAWINGS

Various aspects of the disclosed surgical stapling device are described herein below with reference to the drawings, wherein.

DETAILED DESCRIPTION

Figure 1:
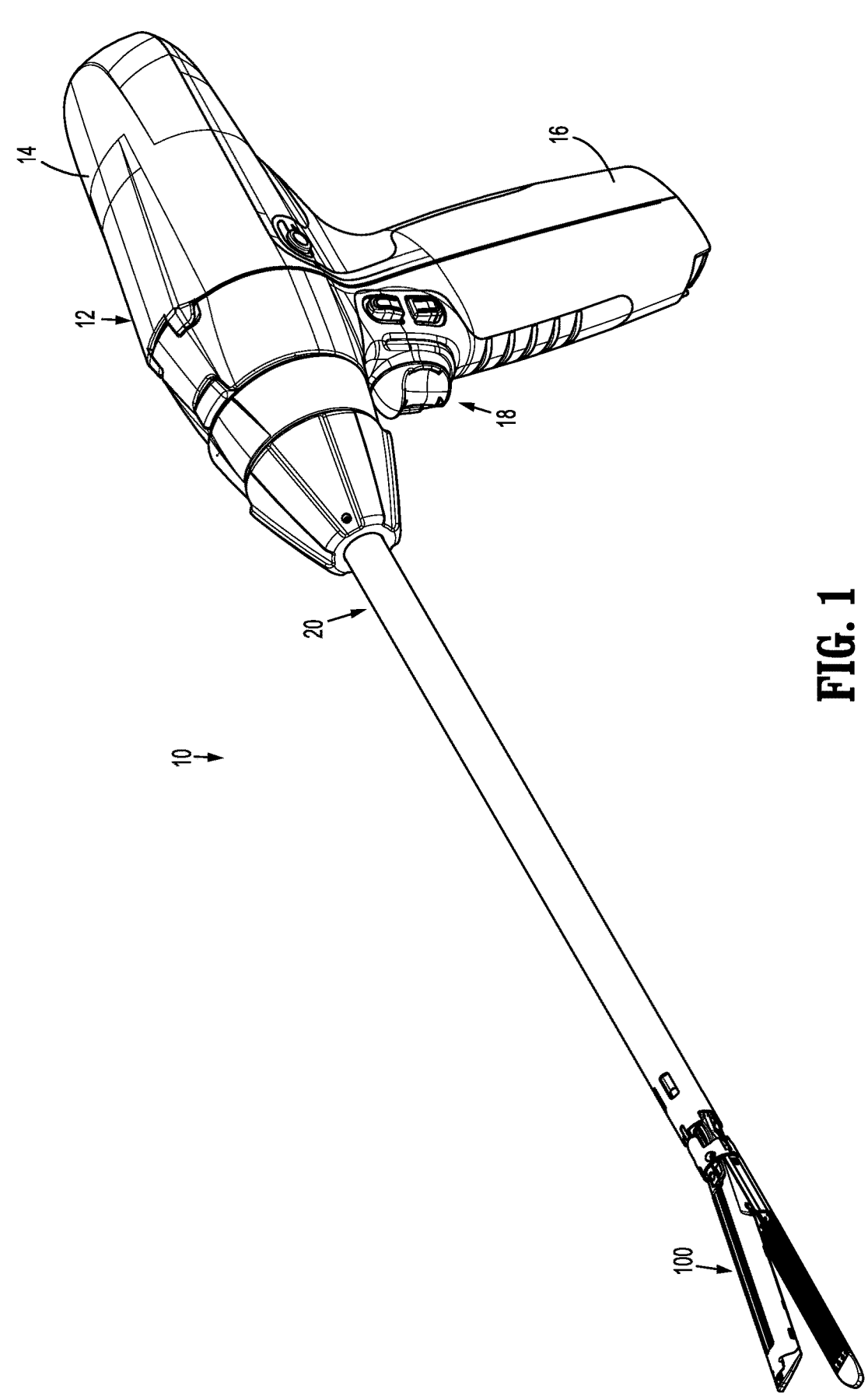
FIG. 1 is a side perspective view of a surgical stapling device according to aspects of the disclosure including a handle assembly, an adapter assembly, and an end effector with the end effector in an open, non-articulated position.

The disclosed surgical stapling device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the device in its customary manner, while the term "distal" is used generally to refer to that portion of the device that is farther from the clinician during use of the device in its customary manner. The term "endoscopic" is used generally to refer to endoscopic, laparoscopic, arthroscopic, and/or any other procedure conducted through a small diameter incision or cannula, and the term "clinician" is used generally to refer to medical personnel including doctors, nurses, surgeons, and support personnel. In addition, directional terms such as front, rear, upper, lower, top, bottom, and similar terms are used to assist in understanding the description and are not intended to limit the disclosure.

This disclosure is directed to a powered stapling device that includes an adapter assembly having an outer tube, a shifter mechanism, an articulation gear, and a rotate gear. The rotate gear is secured to the outer tube such that rotation of the rotate gear causes rotation of the outer tube. The shifter mechanism includes a shifter shaft that supports a shifter gear. The shifter shaft is movable to move the shifter gear between a rotate position in which rotation of the articulation gear causes rotation of the rotate gear and an articulate position in which the shifter gear prevents or locks rotation of the rotate gear and the outer tube.

Figure 2:
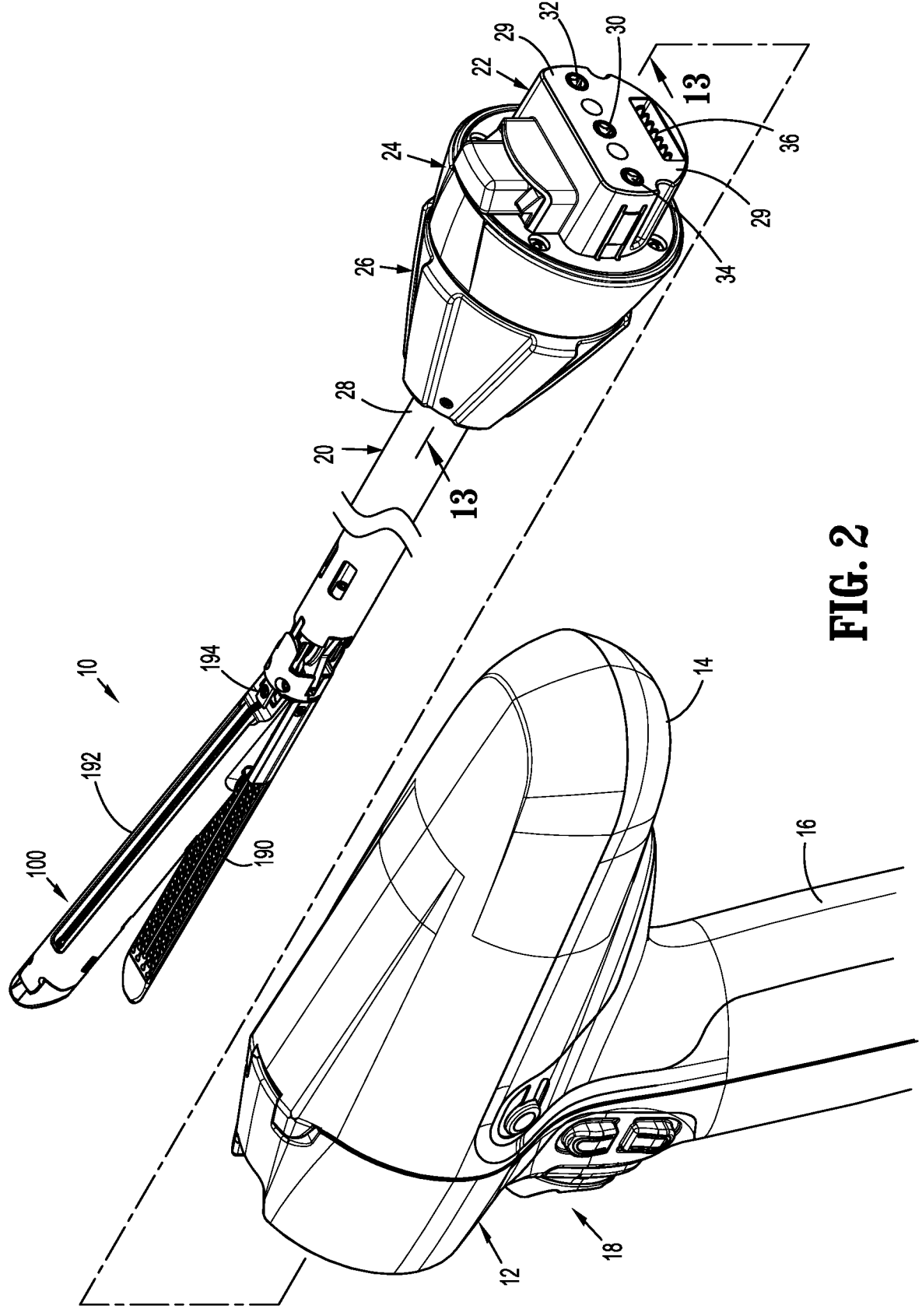
FIG. 2 is a side perspective view of the surgical stapling device shown in FIG. 1 with the adapter assembly separated from the handle assembly.

FIGS. 1 and 2 illustrate a surgical stapling device 10 including a handle assembly 12, an adapter assembly 20 coupled to the handle assembly 12, and an end effector 100 pivotably coupled to the adapter assembly 20. While the depicted surgical stapling device 10 may be configured to fire staples, it is contemplated that the surgical stapling device 10 may be adapted to fire any other suitable fastener such as clips and two-part fasteners. Additionally, while the figures depict a linear surgical stapling device 10, it is envisioned that certain components described herein may be adapted for use in other types of endoscopic surgical instruments including non-linear surgical stapler loading units, endoscopic forceps, graspers, dissectors, other types of surgical stapling instruments, and powered vessel sealing and/or cutting devices.

The handle assembly 12 incudes a housing 14 that defines a stationary grip 16 and supports actuator buttons 18 for controlling activation of motors (not shown) supported within the housing 14. The motors drive the various functions of the surgical stapling device 10 including approximation, firing, rotation, and articulation. For a detailed description of an exemplary handle assembly, reference may be made to U.S. Patent Application Publication No. 2015/0157320, filed on Nov. 21, 2014, and U.S. Patent Application Publication No. 2016/0310134, filed on Apr. 12, 2016.

Figure 3:
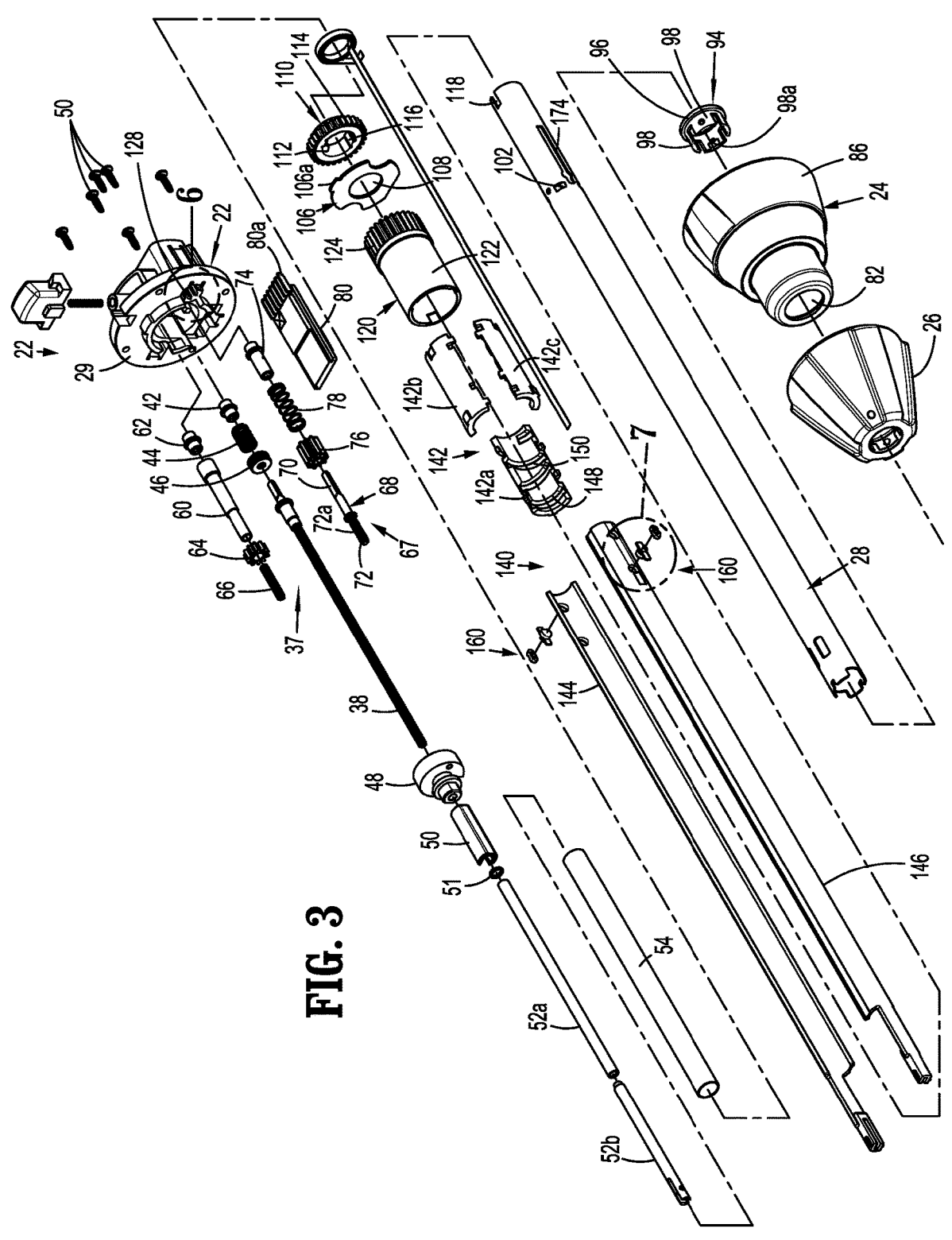
FIG. 3 is an exploded, side perspective view of the adapter assembly of the surgical stapling device shown in FIG. 2.
Figures 4, 5:
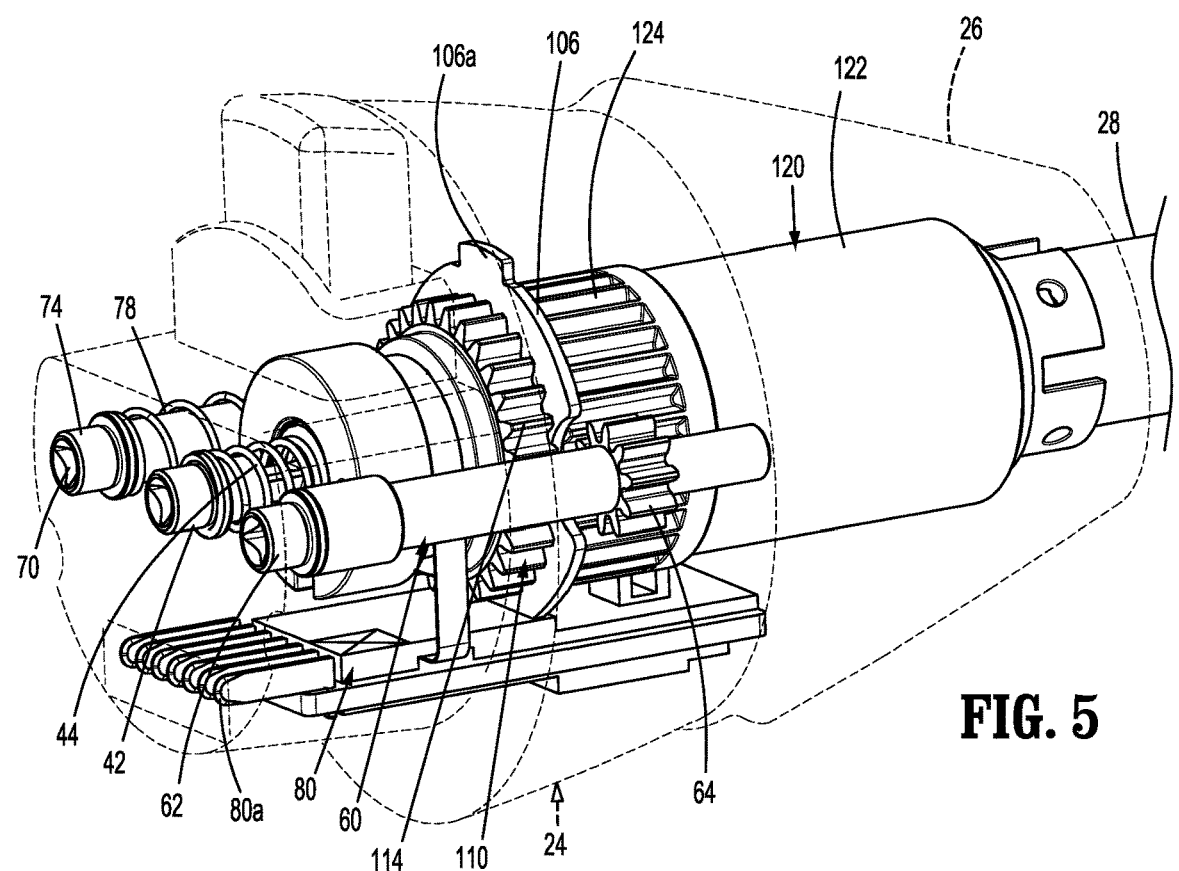
FIG. 4 is a perspective view from one side of a proximal portion of the adapter assembly with a knob housing and coupling mechanism shown in phantom.
FIG. 5 is a perspective view from the other side of the proximal portion of the adapter assembly with a knob housing and coupling mechanism shown in phantom.
Figures 6, 7, 8:
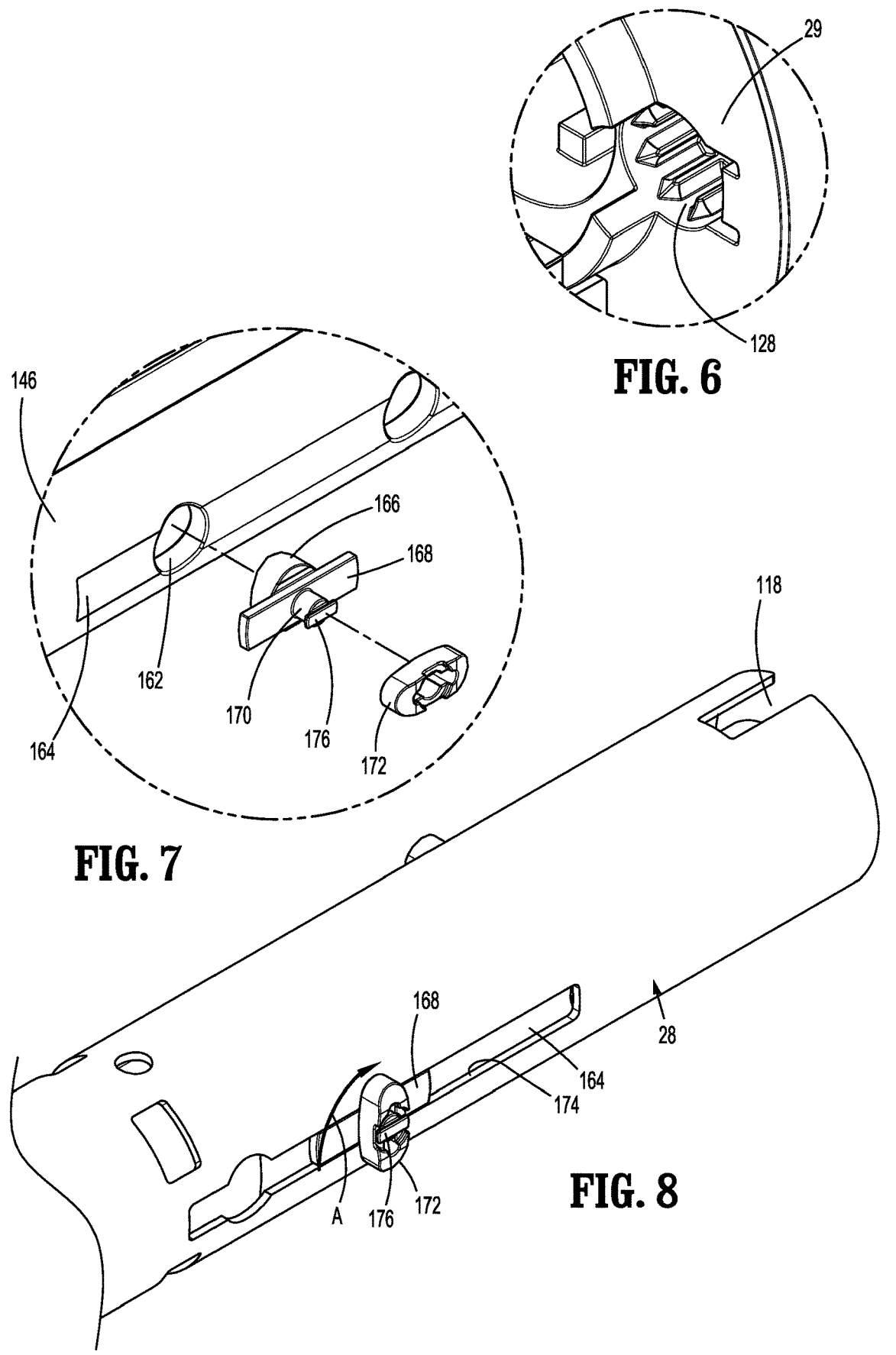
FIG. 6 is an enlarged view of the indicated area of detail shown in FIG. 3.
FIG. 7 is an enlarged view of the indicated area of detail shown in FIG. 3.
FIG. 8 is a side perspective view of a proximal portion of an outer tube and articulation mechanism of the adapter assembly shown in FIG. 3.
Figure 9:
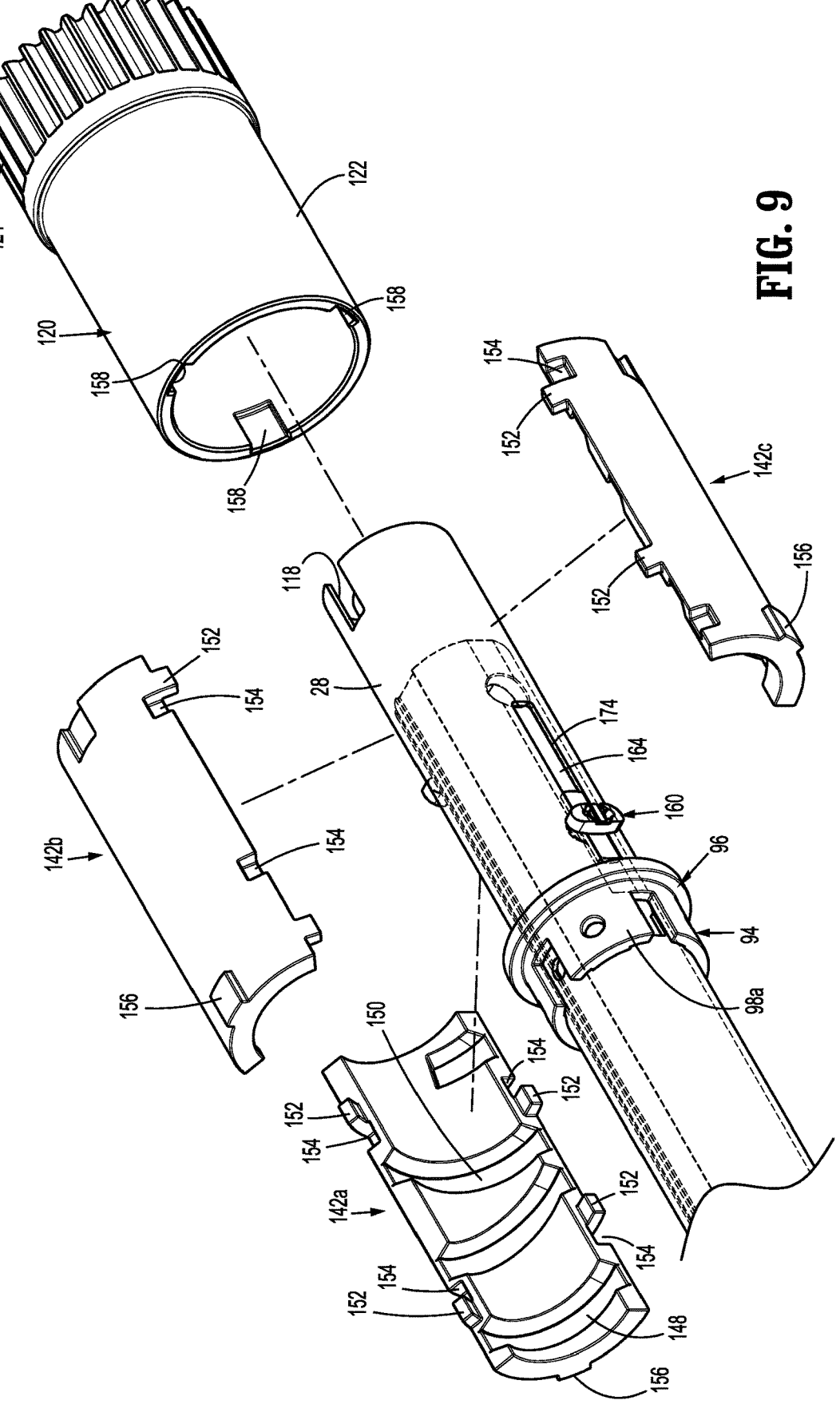
FIG. 9 is an exploded view of a proximal portion of an articulation mechanism of the adapter assembly shown in FIG. 2.

FIGS. 2-13 illustrate the adapter assembly 20 of the surgical stapling device 10 which includes a coupling assembly 22, an outer housing 24, a rotation member 26, and an outer tube 28. The coupling assembly 22 is configured to be coupled to the handle assembly 12 and includes, inter alia, a body 29 (FIG. 13) that defines a first centrally positioned through bore 30, a second bore 32, a third bore 34, and a cavity 36. In aspects of the disclosure, the body 29 is non-rotatably, but releasably, coupled to the handle assembly 12 of the surgical stapling device 10 (FIG. 1). The first through bore 30 (FIG. 13) receives a drive screw 38 that supports a first coupler 42 that is configured to couple the drive screw 38 to a motor drive shaft (not shown) in the handle assembly 12 to provide rotary motion to the drive screw 38. In aspects of the disclosure, the first coupler 42 is spring loaded about the drive screw 38 by a biasing member 44 (FIG. 3) and a proximal end of the drive screw 38 is supported within the body 29 of the coupling assembly 22 by a thrust bearing 46 (FIG. 3). In some aspects of the disclosure, the thrust bearing 46 and the proximal end of the drive screw 38 are supported within a bushing 48 that is secured to the body 29 of the coupling assembly 22 by screws 50 (FIG. 3).

The drive assembly 37 (FIG. 3) of the adapter assembly 20 includes the drive screw 38, a drive member 50, drive links 52a and 52b, and a containment sleeve 54. The drive member 50 defines a threaded bore 50a (FIG. 13) that receives and is engaged with the drive screw 38 such that rotation of the drive screw 38 causes longitudinal movement of the drive member 50 about the drive screw 38 within the containment sleeve 54. The drive links 52a and 52b are tubular and receive the drive screw 38 at a position distal of the drive member 50. The drive link 52b is coupled to the drive link 52a. The drive member 50 includes a distal portion that is engaged with a proximal portion of the drive link 52a such that longitudinal movement of the drive member 50 about the drive screw 38 causes longitudinal movement of the drive links 52a, 52b within the outer tube 28. The drive link 52b is coupled to a firing member 194

(FIG. 11) that is received within the end effector 100 such that distal movement of the drive link 52b causes distal movement of the firing member 194 to approximate and fire the end effector 100. In aspects of the disclosure, the drive member 50 defines an internally located annular groove that receives an O-ring seal 51 (FIG. 13) that is positioned about a proximal portion of the drive link 52a.

The second bore 32 (FIG. 13) of the body 29 of the coupling assembly 22 supports a drive shaft 60 that has a proximal portion and a distal portion. The proximal portion of the drive shaft 60 is engaged with a second coupler 62 that is configured to couple the drive shaft 60 to a motor drive shaft (not shown) of the handle assembly 12 to provide rotary motion to the drive shaft 60. The distal portion of the drive shaft 60 supports a drive gear 64 (FIG. 3) that rotates with the drive shaft 60. In aspects of the disclosure, the drive shaft 60 can move longitudinally within the second bore 32 (FIG. 13) of the body 29 of the coupling assembly 22 between retracted and advanced positions. In some aspects of the disclosure, the drive shaft 60 is urged towards the retracted position by a biasing member 66.

The third bore 34 (FIG. 13) of the body 29 of the coupling assembly 22 supports a shifter mechanism 67 which includes a shifter shaft 68 and a shifter gear 76. The shifter shaft 68 has a proximal portion 70 and a distal portion 72. The distal portion 72 of the shifter shaft 68 is threaded and the proximal portion 70 supports a third coupler 74 that is configured to couple the shifter shaft 68 to a motor drive shaft (not shown) in the handle assembly 12 to provide rotary motion to the shifter shaft 68. A central portion of the shifter shaft 68 supports a shifter gear 76. The third coupler 74 is spring loaded and is urged proximally by a biasing member 78.

The cavity 36 of the body 29 of the coupling assembly 22 receives a printed control board (PCB) 80 that has contacts 80a that are positioned within the cavity 36. The contacts 80a are positioned to engage contacts within the handle assembly 12 when the adapter assembly 20 is coupled to the handle assembly 12 (FIG. 1) to control operation of the motors within the handle assembly 12 (FIG. 1).

The outer housing 24 of the adapter assembly 20 includes a hollow body 86 that is fixedly secured to the body 29 of the coupling assembly 22 and defines a central through bore 82 that is aligned with the through bore 30 of the body 29 of the coupling assembly 22. The central through bore 82 is stepped and has a diameter that decreases in the distal direction. In aspects of the disclosure, the hollow body 86 of the outer housing 24 of the adapter assembly 20 defines a distal shoulder 90a and a proximal shoulder 90b.

The rotation member 26 is rotatably coupled to the outer housing 24 of the adapter assembly 14 and fixedly coupled to the outer tube 28 by an attachment ring 94 (FIG. 3). The attachment ring 94 includes an annular base 96 and a plurality of distally extending resilient fingers 98. Each of the fingers 98 includes an inwardly extending tab 98a. The attachment ring 94 is received about the outer tube 28. The outer tube 28 defines spaced openings 102 that receive the tabs 98a of the fingers 98 of the attachment ring 94 to secure the attachment ring 94 to the proximal portion of the outer tube 28. The base member 96 has a distally facing annular shoulder 96a that is in abutting relation to the distal shoulder 90a of the hollow body 86 of the outer housing 24 to rotatably support the outer tube 28 within the central through bore 82 of the outer housing 24.

The adapter assembly 20 includes a mounting plate 106 that is secured within the body 29 of the coupling assembly 22 and defines a central opening 108 that receives the proximal portion of the outer tube 24. In aspects of the disclosure, the mounting plate 106 includes one or more tabs 106*a* that are received in slots (not shown) defined within the body 29 of the coupling assembly 22 to fixedly secure the mounting plate 106 within the body 29 of the coupling assembly 22.

The adapter assembly 20 includes a rotate gear 110 (FIG. 3) that is positioned adjacent a proximal face of the mounting plate 106. The rotate gear 110 defines a circular opening 112 and includes outer gear teeth 114 and inner tabs 116 that extend into the circular opening 112. The proximal portion of the outer tube 28 is received within the circular opening 112 of the rotate gear 110 and defines notches 118 (FIG. 3) that receive the inner tabs 116 of the outer tube 28 to secure the rotate gear 110 to the outer tube 28.

The adapter assembly 20 also includes an articulation gear 120 that is supported within the central through bore 82 of the hollow body 86 of the outer housing 24 of the adapter assembly 20. The articulation gear 120 is rotatably supported within the hollow body 86 of the outer housing 24 and includes a cylindrical body 122 and gear teeth 124 positioned about a proximal portion of the cylindrical body 122. The gear teeth 124 of the articulation gear 120 are positioned adjacent to a distal face of the mounting plate 106 and are engaged with the drive gear 64 such that rotation of the drive gear 64 rotates the articulation gear 120 within the outer housing 24 of the adapter assembly 20.

FIGS. 3-6 illustrate the shifter mechanism 67 which includes the shifter shaft 68 and the shifter gear 76 which is secured to the central portion of the shifter shaft 68. The distal portion 72 of the shifter shaft 68 includes screw threads 72*a* and is received within a threaded bore 130 formed in the hollow body 86 of the outer housing 24 of the adapter assembly 20. When the shifter shaft 68 is rotated by a motor (not shown) supported within the handle assembly 12 (FIG. 1), the shifter shaft 68 moves longitudinally in relation to the outer housing 24 between an advanced or rotate position and a retracted or articulate position. In the advanced or rotate position of the shifter shaft 68 (FIG. 13), the shifter gear 76 is engaged with the rotate gear 110 and the articulation gear 120. In the retracted or articulate position, the shifter gear 76 is engaged with the rotate gear 110 and disengaged from the articulation gear 120. The shifter gear 76 is received within a splined opening 128 (FIG. 6) formed in the body 29 of the coupling assembly 22 to prevent rotation of the rotate gear 110 and the outer tube 28 in relation to the handle assembly 12 (FIG. 1) as described in detail below.

FIGS. 3 and 9-12 illustrate an articulation mechanism 140 of the adapter assembly 20 of the stapling device 10 (FIG. 1). The articulation mechanism 140 includes a barrel cam 142, a first link extension 144, a second link extension 146, a first articulation link 147, and a second articulation link 149. The barrel cam 142 is received within the cylindrical body 122 of the articulation gear 120 and defines a first cam channel 148 and a second cam channel 150. In aspects of the disclosure, the barrel cam 142 is formed from barrel cam portions 142*a-c* that are secured together within the articulation gear 120 to define a cylinder. In aspects of the disclosure, each of the cam portions 142*a-c* of the barrel cam 142 includes tabs 152 and defines slots 154 that mesh to secure the cam portions 142*a-c* together. In certain aspects of the disclosure, each of the cam portions 142*a-c* includes an outwardly extending projection 156 that is received within a recess 158 (FIG. 9) defined along an inner surface of the articulation gear 120 to retain the barrel cam 142 at a fixed position within the articulation gear 120.

The first and second link extensions 144, 146 have elongated semi-circular configurations and are slidably supported on and about the containment sleeve 54 (FIG. 3) of the adapter assembly 20 within the outer tube 28. The proximal portion of each of the first and second link extensions 144, 146 supports a cam member 160 that extends outwardly from the first and second link extension 144, 146. In certain aspects of the disclosure, the proximal portion (FIG. 7) of each of the first and second articulation link extensions 144, 146 defines a circular transverse bore 162 and a rectangular channel 164, and the cam member 160 includes a circular body portion 166, a rectangular body portion 168, a post 170, and a follower 172 that is releasably coupled to the post 170. The circular body portion 166 of the cam members 160 are received within the transverse bores 162 of the first or second articulation link extensions 144, 146 and the rectangular body portions 168 are received within the rectangular channels 164 of the first and second articulation link extensions 144, 146. In aspects of the disclosure, the post 170 extends through an elongate slot 174 formed in the outer tube 28 and the follower 172 is rotatably secured to the post 170. In aspects of the disclosure, the follower 172 has an elongate configuration and the post 170 supports a retaining member 176 that locks the follower 172 onto the post 170 for movement along an outer surface of the outer tube 28 when the follower 172 is rotated about ninety degrees about the post 170 in the direction of arrow "A" in FIG. 8. Receipt of the posts 170 of the cam members 160 within the elongate slots 174 of the outer tube 28 secures the first and second link extensions 144, 146 to the outer tube 28 to prevent rotation of the link extensions 144, 146 in relation to the outer tube 28.

Each of the followers 172 of the cam members 160 is received within one of the first or second cam channels 148, 150 of the barrel cam 142. The first and second cam channels 148, 150 are configured such that rotation of the barrel cam 142 causes the first link extension 144 to move longitudinally within the outer tube 28 in a first direction and to simultaneously move the second articulation extension 146 longitudinally within the outer tube 28 in a second opposite direction.

Figure 10:
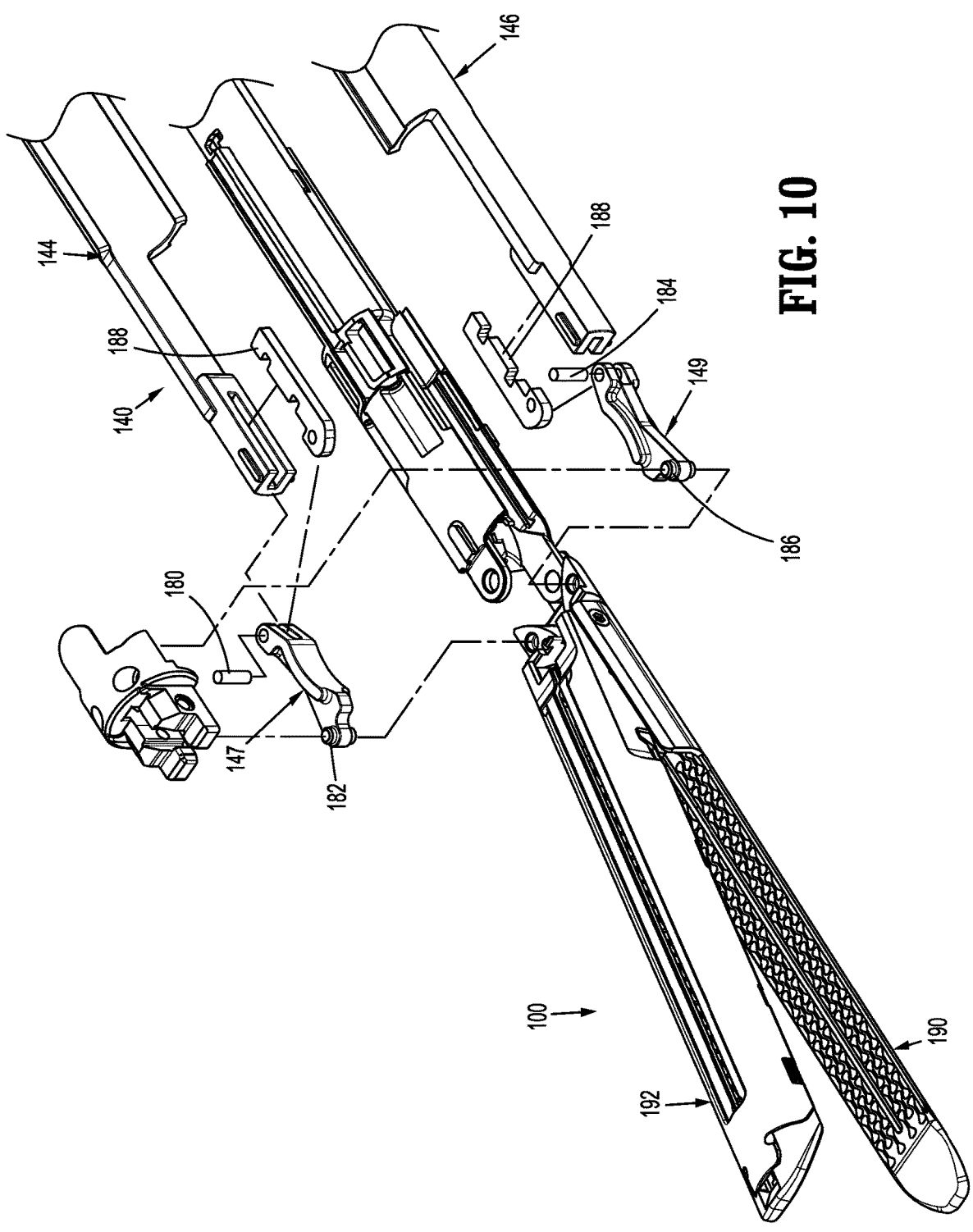
FIG. 10 is an exploded, side perspective view of the distal portion of the adapter assembly and the end effector of the surgical stapling device shown in FIG. 2 with an outer tube of the adapter assembly removed.
Figures 11, 12:
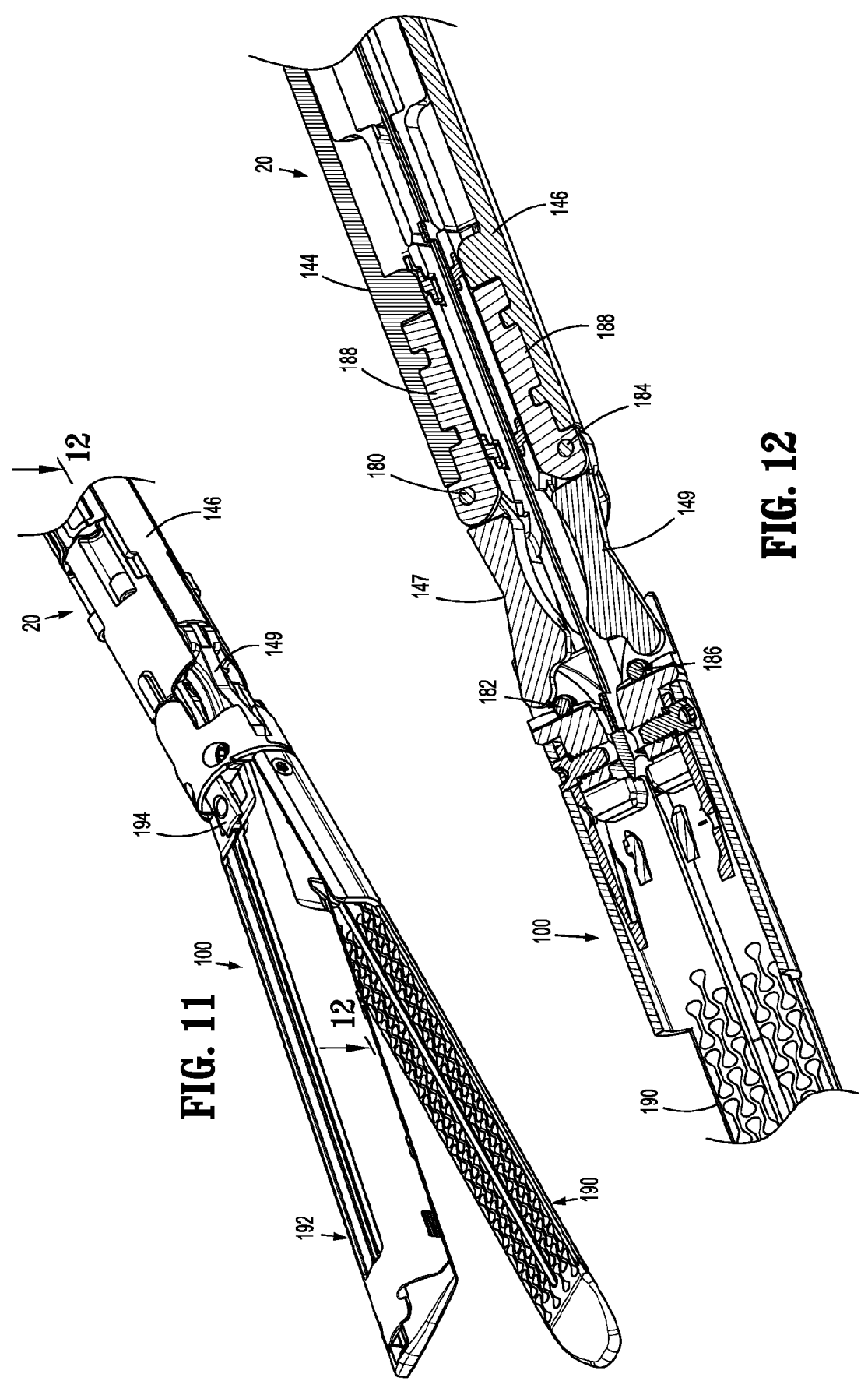
FIG. 11 is a side perspective view of the distal portion of the adapter assembly and the end effector of the surgical stapling device shown in FIG. 2 with the outer tube of the adapter assembly removed.
FIG. 12 is a cross-sectional view taken along section line 12-12 of FIG. 11.
Figure 13:
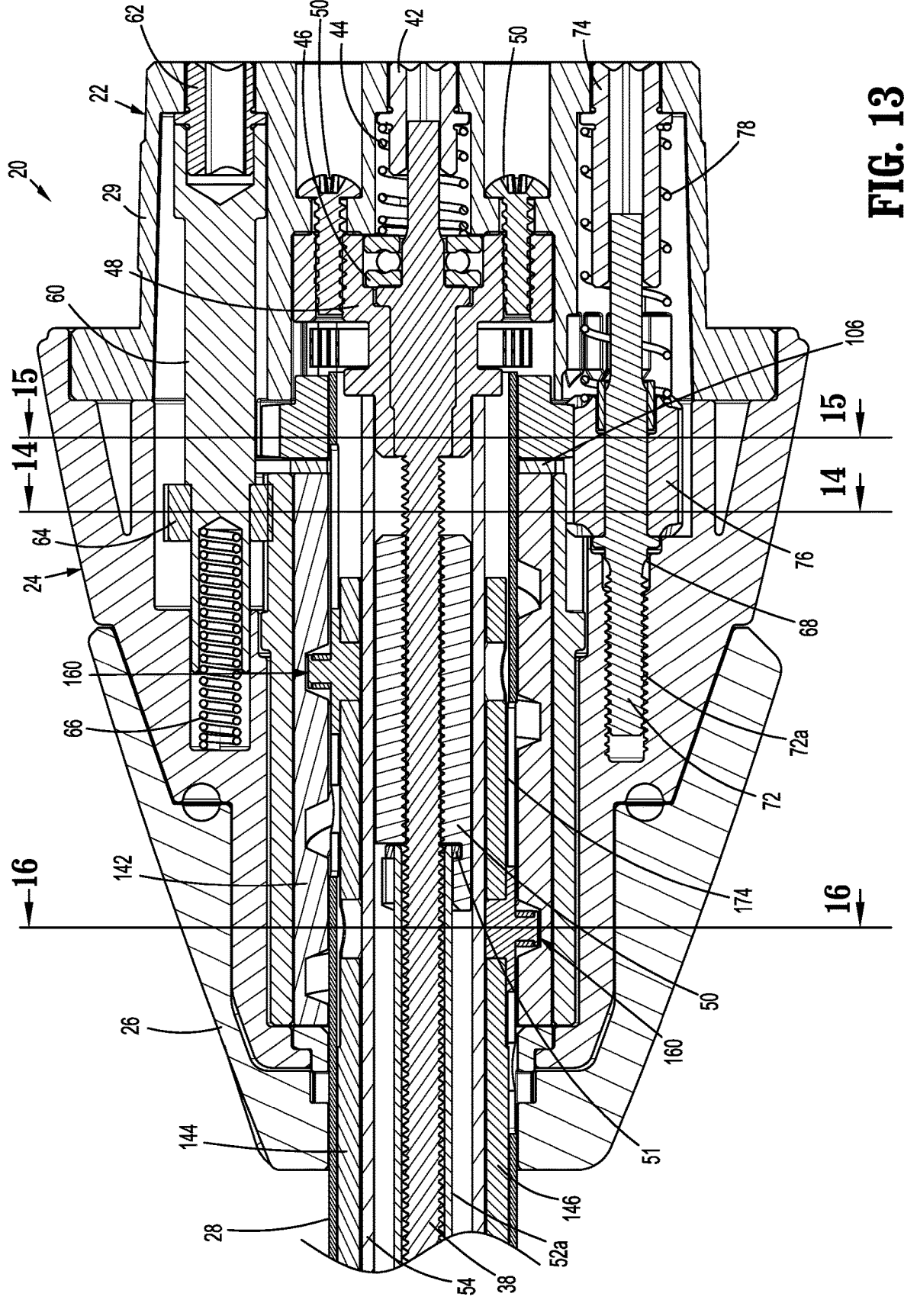
FIG. 13 is a cross-sectional view taken along section line 13-13 of FIG. 2 illustrating the proximal portion of the adapter assembly in a rotation mode.

FIGS. 10-12 illustrate the distal portion of the articulation mechanism 140. The distal portion of the link extensions 144, 146 are pivotally coupled to the end effector 100 by the articulation links 147, 149. In aspects of the disclosure, the distal portion of the first link extension 144 is pivotably coupled to the articulation link 147 by a pivot pin 180, and the distal portion of the articulation link 147 is pivotably coupled to the end effector 100 by a pivot member 182. Similarly, the distal portion of the articulation link extension 146 is pivotably coupled to the articulation link 149 by a pivot pin 184, and the distal portion of the articulation link 149 is pivotably coupled to the end effector 100 by a pivot member 186. In aspects of the disclosure, the pivot members 180, 182, 184, and 186 can be integrally formed with the articulation links 147 and 149 or formed separately from the articulation links 147, 149. In some aspects of the disclosure, the distal portion of the first and second link extensions 144, 146 can be coupled to the proximal portions of the articulation links 147, 149 by connecting links 188. The connecting links 188 can be fixedly secured to the distal portions of the first and second link extensions 144, 146 and pivotably coupled to the articulation links 147, 149 by the pivot members 180, 184.

In aspects of the disclosure, the end effector 100 includes an anvil assembly 190 and a cartridge assembly 192, and the drive link 52*b* is coupled to a firing member 194 (FIG. 11).

When the drive link 52*b* is driven distally by the drive screw 38, the firing member 194 is movable through the end effector 100 to initially move the end effector 100 from an open position to a clamped position and subsequently to move through the end effector 100 to eject staples from the cartridge assembly 192. In some aspects of the disclosure, the firing member 194 has an I-beam configuration.

Although not described in detail herein, the end effector 100 is pivotably coupled to the distal portion of the adapter assembly 20 about an articulation axis that is transverse to a longitudinal axis of the adapter assembly 20. When the first and second link extensions 144, 146 are moved longitudinally in response to rotation of the barrel cam 142, the end effector 100 is pivoted about the articulation axis in one direction or the other depending on the direction of rotation of the barrel cam 142.

FIGS. 13-17 illustrate the proximal portion of the adapter assembly 20 with the shifter shaft 76 of the shifter mechanism 67 in the advanced or rotate position. When the shifter mechanism 67 of the adapter assembly 20 is in the rotate position and the articulate position, the drive gear 64 of the drive shaft 60 is engaged with the gear teeth 124 of the articulation gear 120.

Figures 14, 15:
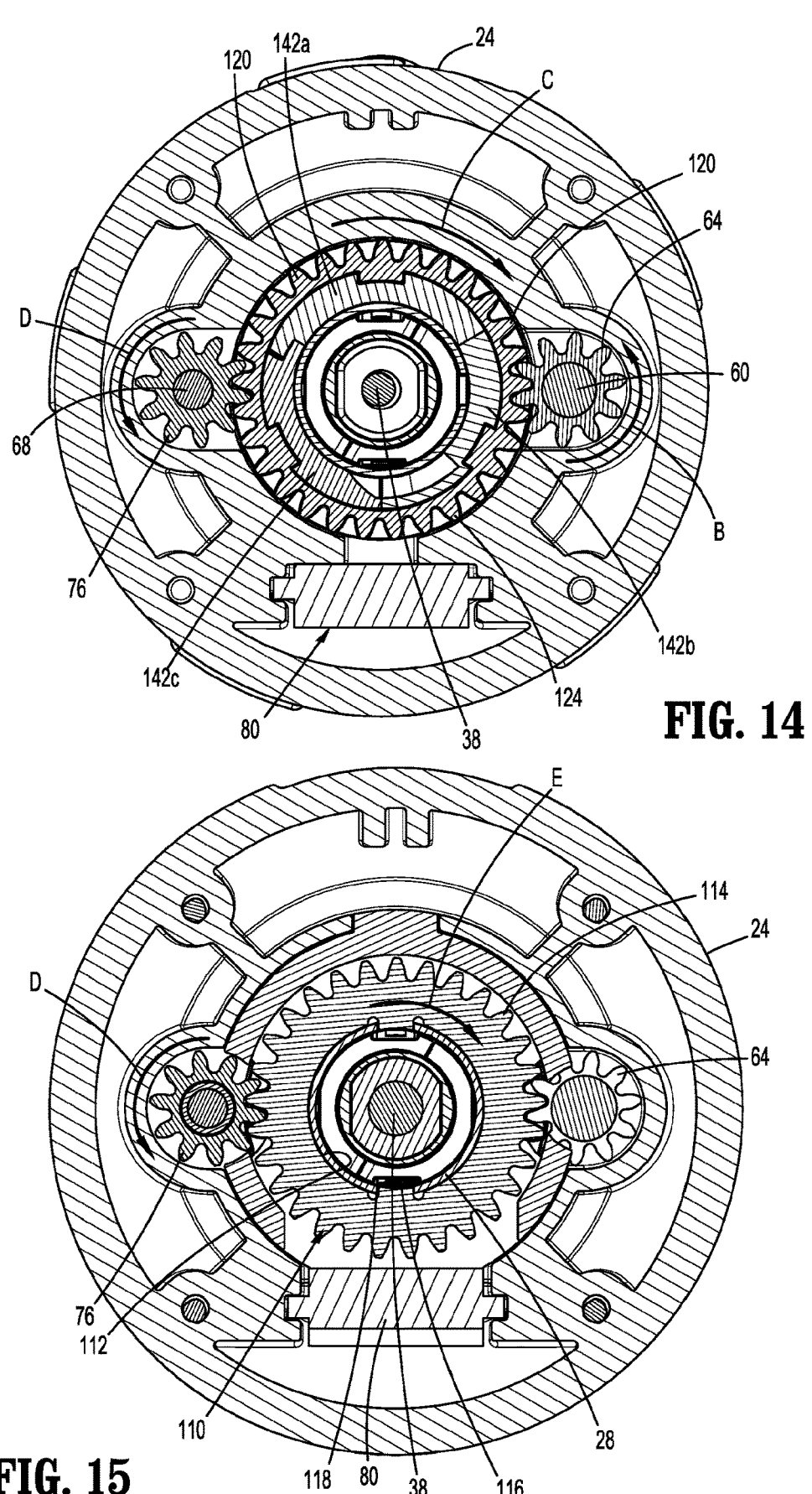
FIG. 14 is a cross-sectional view taken along section line 14-14 of FIG. 13.
FIG. 15 is a cross-sectional view taken along section line 15-15 of FIG. 13.
Figures 16, 17:
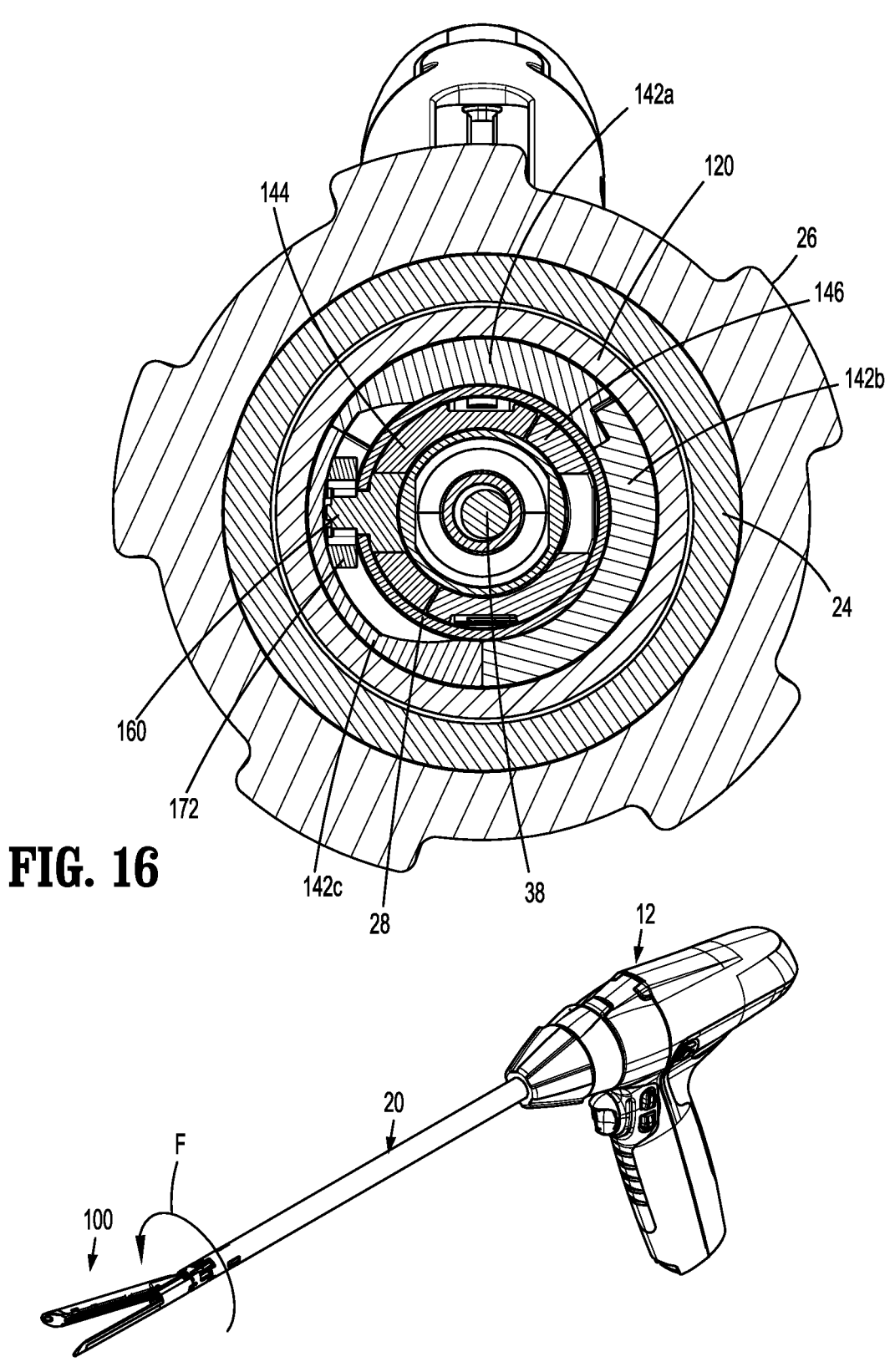
FIG. 16 is a cross-sectional view taken along section line 16-16 of FIG. 13.
FIG. 17 is a side perspective view of the surgical stapling device shown in FIG. 1 as the distal portion of the adapter assembly and the tool assembly are rotated.

When the handle assembly 12 is activated to rotate the drive gear 64 in the direction of arrow "B" in FIG. 14 with the shifter mechanism 67 is in the rotate position, the articulation gear 120 is rotated about the longitudinal axis of the adapter assembly 20 in the direction of arrow "C" in FIG. 14. As described above, in the rotate position, the shifter gear 76 of the shifter mechanism 67 is engaged with the rotate gear 110 and the articulation gear 120. As such, when the drive gear 64 is rotated with the drive shaft 60 in the direction of arrow "B" in FIG. 14, the drive gear 64 rotates the articulation gear 120 in the direction of arrow "C", the articulation gear 120 rotates the shifter gear 76 in the direction of arrow "D" in FIG. 15, and the shifter gear 76 rotates the rotate gear 110 in the direction of arrow "E". The rotate gear 110 is coupled to the outer tube 28 (FIG. 16) such that when the rotate gear 110 rotates in the direction of arrow "E" in FIG. 15, the outer tube 28 and the articulation mechanism 140 which is rotatably fixed to the outer tube 28 by the posts 170 of the cam member 160 rotate with the articulation gear 120 about the longitudinal axis of the adapter assembly 20. Since the articulation mechanism 140 rotates with the articulation gear 120, there is no relative movement between the barrel cam 142 and the articulation mechanism 140. Thus, when the shifter mechanism 67 is in the rotate position and the drive gear 64 is rotated with the drive shaft 60, the outer tube 28 of the adapter assembly 20 is rotated with the end effector 100 in the direction of arrow "F" in FIG. 17 about the longitudinal axis of the adapter assembly 20. The end effector 100 is not articulated in the rotate position of the shifter mechanism 67.

Figure 18:
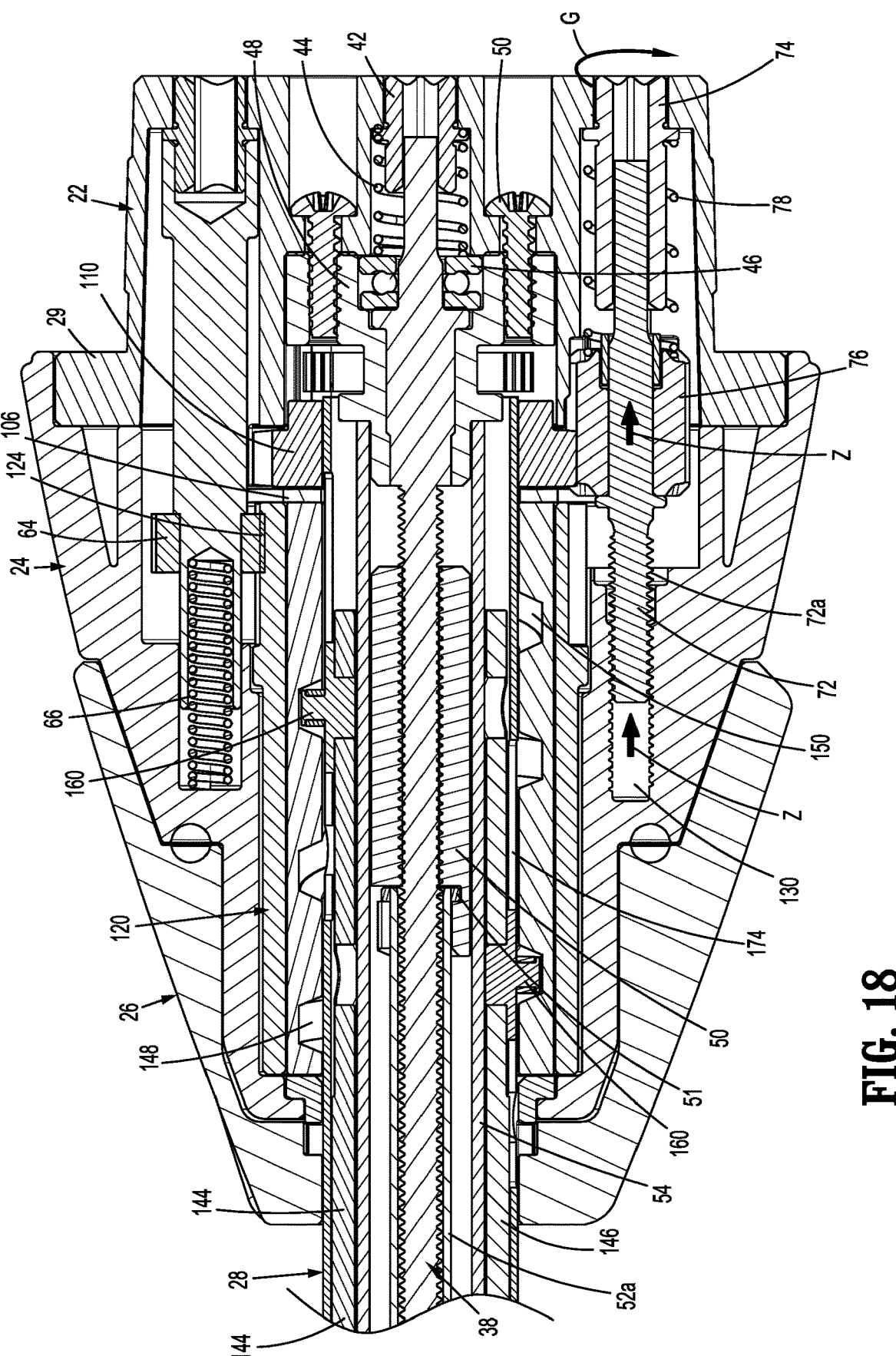
FIG. 18 is a cross-sectional view taken through the proximal portion of the adapter assembly as the adapter assembly is moved from the rotation mode to an articulation mode.

FIG. 18 illustrates the proximal portion of the adapter assembly 20 as the shifter mechanism 67 is moved from the rotate position to the articulate position. When the handle assembly 12 is activated to rotate the shifter shaft 68 in the direction indicated by arrow "G" in FIG. 18, the threaded distal portion 72 of the shaft 68 rotates within the threaded bore 130 of the outer housing 24. As the shifter shaft 68 rotates in the direction of arrow "G", the shifter shaft 68 moves in the direction of arrows "Z" to the articulate position. In the articulate position, the shifter gear 76 disengages from the articulation gear 120 and moves into the splined opening 128 (FIG. 6) defined in the body 29 of the coupling assembly 22. The shifter gear 76 remains engaged with the rotate gear 110. Receipt of the rotate gear 110 within the splined opening 128 of the body 29 of the coupling assembly 22 prevents or locks rotation of the rotate gear 110 and rotation of the outer tube 28 in relation to the body 29 of the coupling assembly 22. It is noted that the drive gear 64 of the drive assembly 67 remains engaged with the articulation gear 120.

Figure 19:
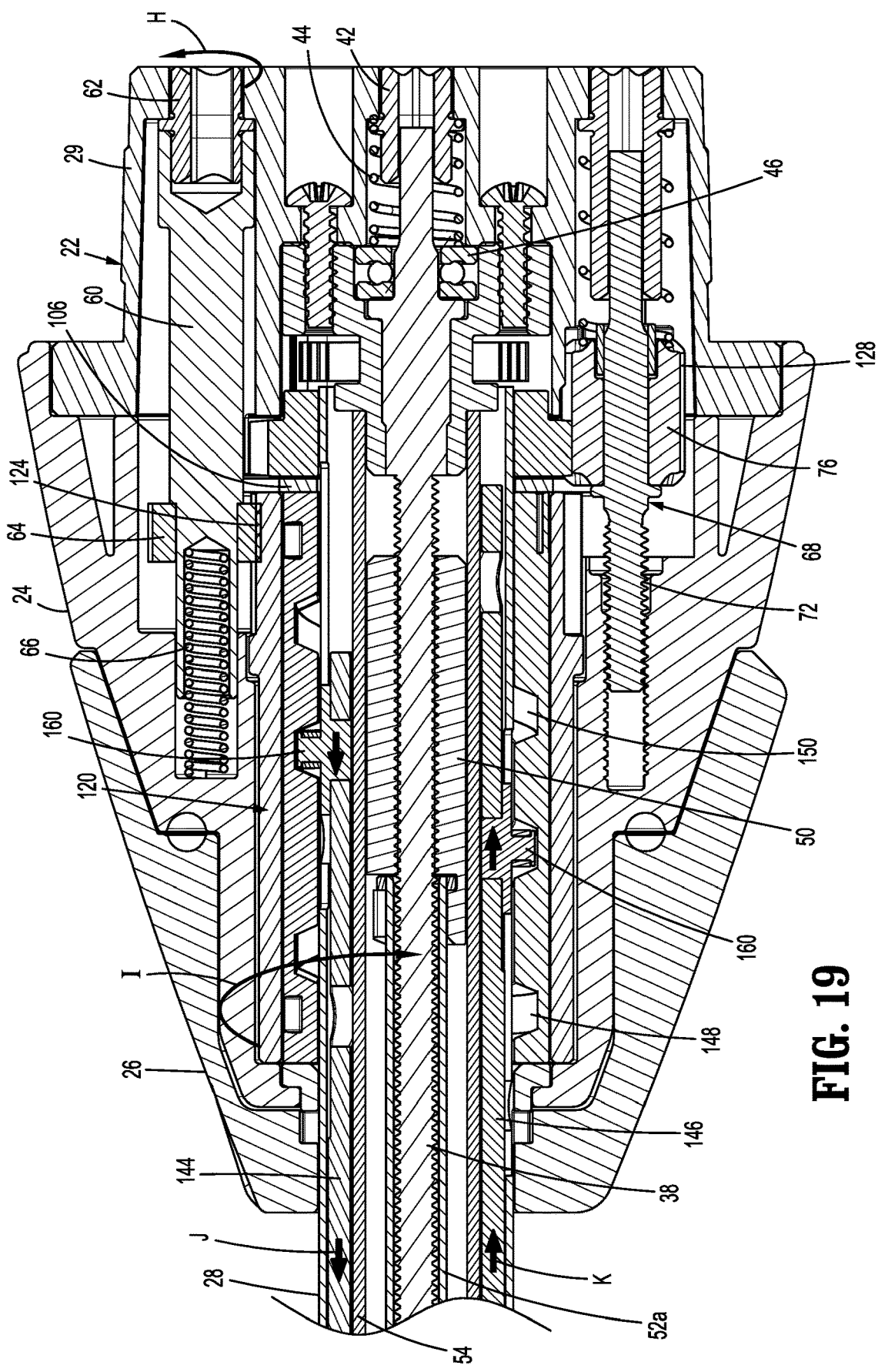
FIG. 19 is a side cross-sectional taken through the proximal portion of the adapter assembly as the adapter assembly with the adapter assembly in the articulation mode as the end effector is articulated.

FIG. 19 illustrates the proximal portion of the adapter assembly 20 with the shifter assembly 67 in the articulate position as the drive gear 64 is rotated in the direction of arrow "H". When the drive gear 64 is rotated in the direction of arrow "H", the articulation gear 120, which includes gear teeth 124 engaged with the drive gear 64, rotates in the direction of arrow "I". As described above, the rotate gear 110 and the outer tube 28 are locked or prevented from rotating in relation to the body 29 of the coupling assembly 22 due to receipt of the shifter gear 76 within the splined opening 128. As the articulation gear 120 rotates in the direction of arrow "I", the barrel cam 142 which is fixedly secured within the articulate gear 120 rotates in the direction of arrow "I". As the barrel cam 142 rotates, the cam members 160 move within the cam channels 148, 150 of the barrel cam 142 to move the first link extension 144 in the direction of arrow "J" and the second link extension 146 in the direction of arrow "K".

Figure 20:
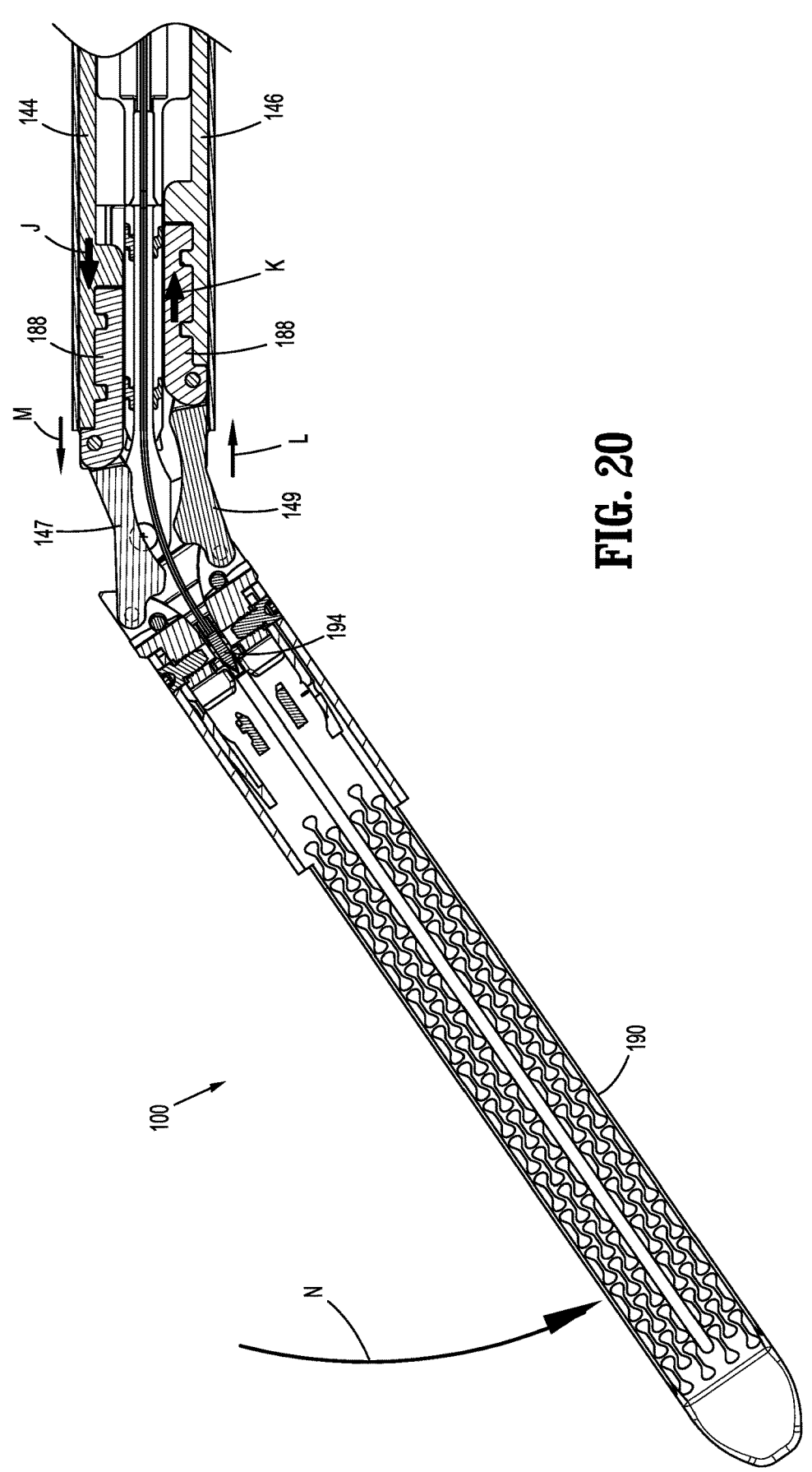
FIG. 20 is a cross-sectional view of the distal portion of the surgical stapling device shown in FIG. 1 as the end effector is articulated in a first direction.
Figures 21, 22:
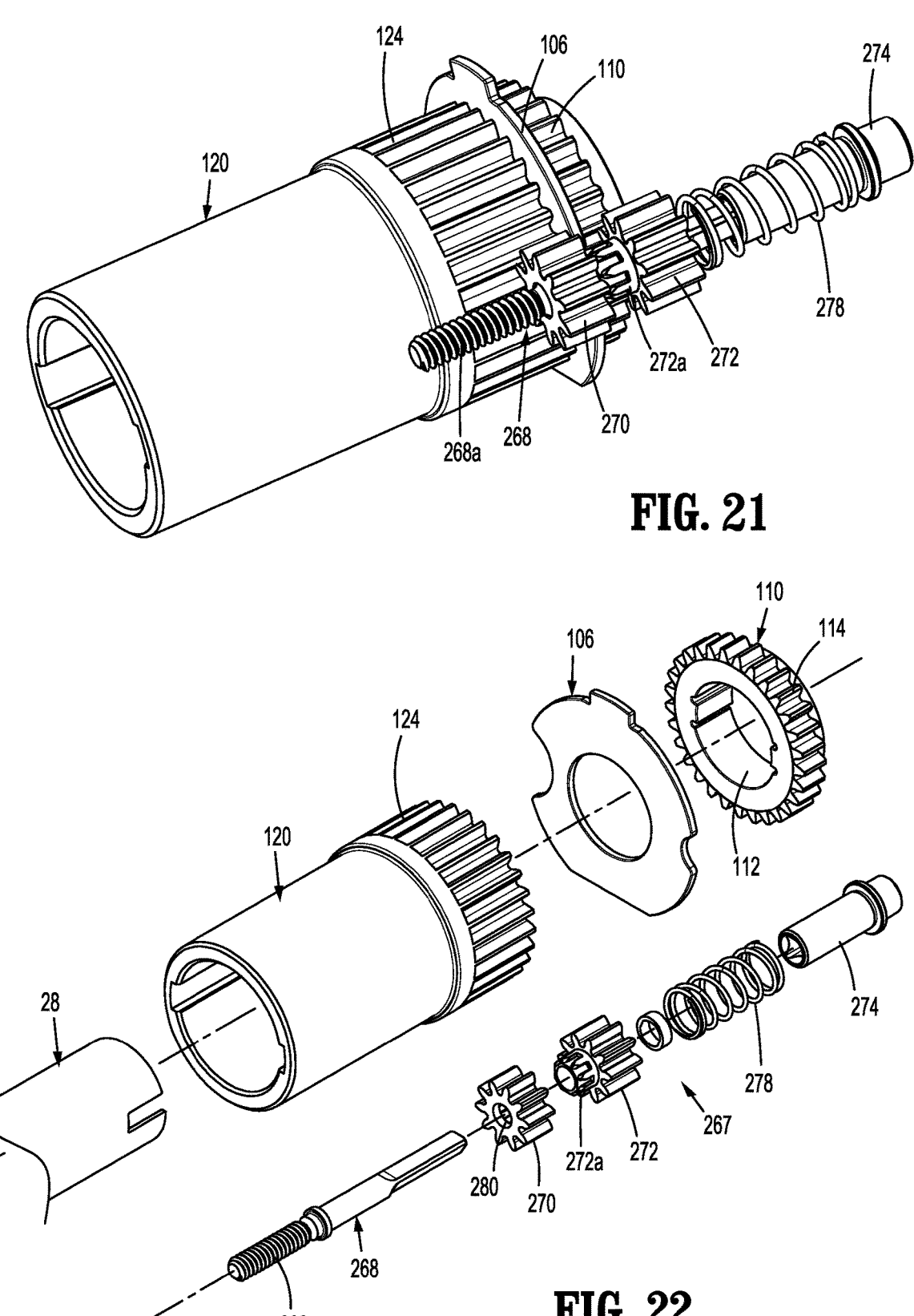
FIG. 21 is a side perspective view of a portion of the adapter assembly shown in FIG. 1 with an alternate version of a rotation gear lock.
FIG. 22 is an exploded view of the portion of the adapter assembly shown in FIG. 21.

FIG. 20 illustrates the end effector 100 as the first link extension 144 moves in the direction of arrow "J" and the second link extension 146 moves in the direction of arrow "K". When the first link extension 144 moves in the direction of arrow "J" and the second link extension 146 moves in the direction of arrow "K", the first articulation link 147 is pulled proximally in the direction of arrow "L" and the second articulation link 149 is moved distally in the direction of arrow "M" to pivot the end effector 100 in the direction of arrow "N". Although the end effector 100 is shown articulating in a first direction, the drive gear 64 can be driven in an opposite direction to articulate the end effector 100 in an opposite direction.

FIGS. 21-24 illustrate an alternate version of the shifter mechanism of the adapter assembly of the stapling device shown in FIG. 1 shown generally as shifter mechanism 267 in association with components as described above including the outer tube 28, the articulation gear 120, the mounting plate 106, and the rotate gear 110. The shifter mechanism 267 includes a shifter shaft 268, an articulate pinion 270, a shifter gear 272, a coupler 274, and a biasing member 278. The coupler 274 functions in a manner like that of coupler 74 (FIG. 13) and will not be described in further detail herein. The shifter gear 272 is fixedly secured to a central portion of the shifter shaft 268 and rotates with the shifter shaft 268. The shifter gear 272 includes a distally extending splined extension 272*a*. The distal portion 268*a* of the shifter shaft 268 is threaded and is received in a threaded bore 130 (FIG. 18) formed in the hollow body 86 of the outer housing 24 of the adapter assembly 20. Rotation of the shifter shaft 268 causes longitudinal movement of the shifter shaft 268. The articulate pinion 270 defines a splined bore 280 and is rotatably supported about the central portion of the shifter shaft 268 at a position distally of the shifter gear 272. The splined bore 280 of the articulate pinion 270 is configured to receive the splined extension 272*a* of the shifter gear 272 to secure the articulate pinion 270 to the shifter gear 272 such that rotation of the articulate pinion 270 causes corresponding rotation of the shifter gear 272.

The biasing member 278 which may be in the form of a coil spring is positioned between the coupler 274 and the shifter gear 272 and urges the shifter gear 272 towards the articulate pinion 270 such that the splined extension 272*a* of the shifter gear 272 is received within the splined bore 280 of the articulate pinion 270. In aspects of the disclosure, the biasing member 278 can be a coil spring although the use of other types of biasing members is envisioned. In some aspects of the disclosure, the coil spring is positioned about the shifter shaft 268 between the coupler 274 and the shifter gear 272.

Figures 23, 24:
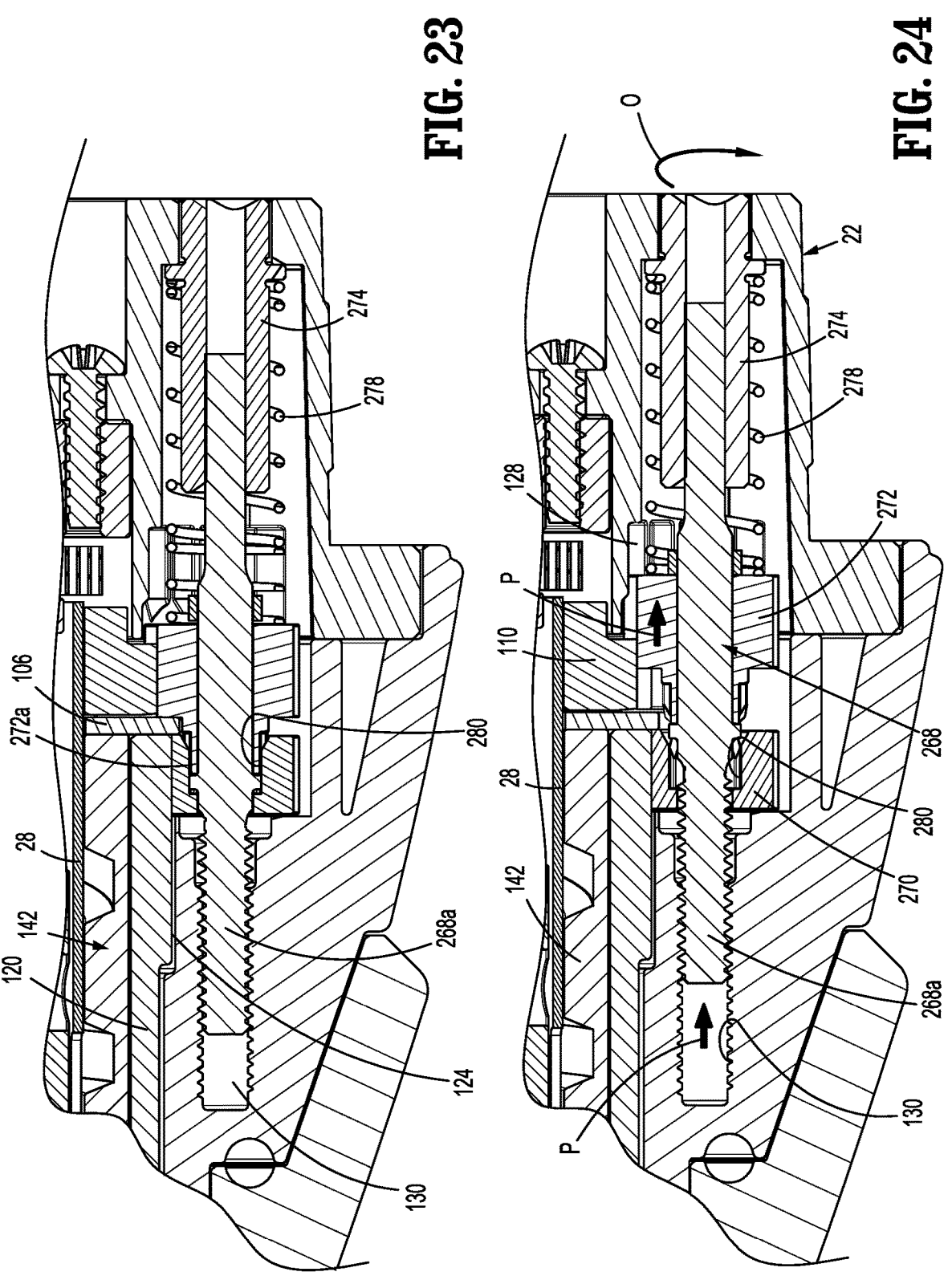
FIG. 23 is a cross-sectional view taken through the adapter assembly including the rotation gear lock shown in FIG. 22 with the adapter assembly in the rotation mode.
FIG. 24 is a cross-sectional view taken through the adapter assembly including the rotation gear lock shown in FIG. 22 as the adapter assembly moves from the rotation mode to the articulation mode.
Figures 25, 26:
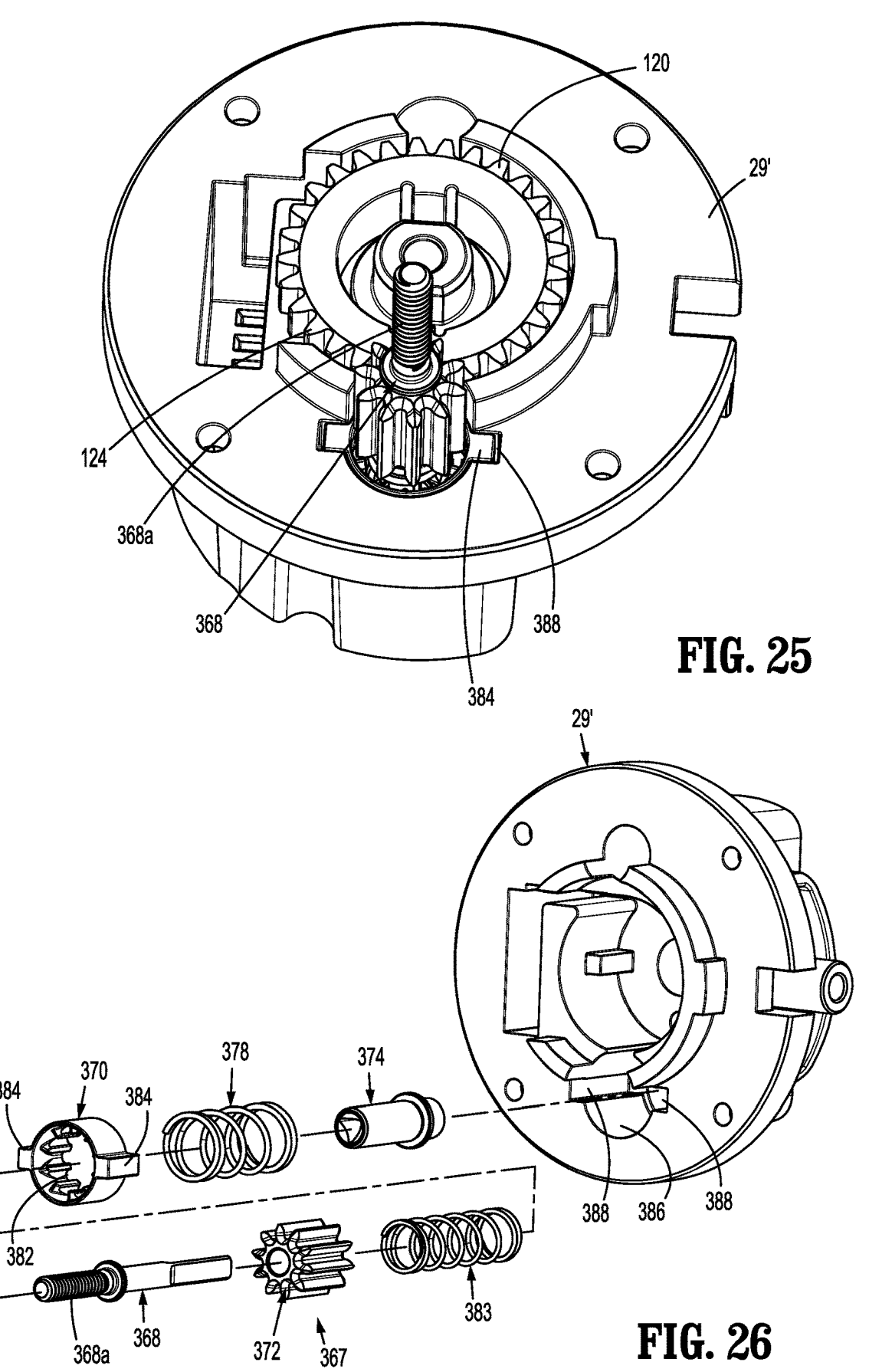
FIG. 25 is a perspective view from the proximal end of portions of the adapter assembly shown in FIG. 1 with another alternate version of a rotation gear lock.
FIG. 26 is an exploded view of the portion of the adapter assembly shown in FIG. 25.

Like the shifter mechanism 67 (FIG. 3), the shifter assembly 267 is movable between an articulate position and a rotate position. FIG. 23 illustrates the shifter assembly 267 in the rotate position. In the rotate position, the splined extension 272a of the of the shifter gear 272 is received within the splined bore 280 of the articulate pinion 270 such that the articulate pinion 270 is rotatably fixed to the shifter gear 272. In addition, the articulate piston 270 is engaged with the teeth 124 of the articulation gear 120 and the shifter gear 272 is engaged with the gear teeth 114 of the rotate gear 110.

As described above (FIG. 3), the gear teeth 124 of the articulation gear 120 are positioned adjacent to the distal face of the mounting plate 106 and are engaged with the drive gear 64 such that rotation of the drive gear 64 rotates the articulation gear 120 within the outer housing 24 of the adapter assembly 20. When the articulation gear 120 rotates, the gear teeth 124 of the articulation gear 120 rotate the articulation pinion 270 which rotates the shifter gear 272. The shifter gear 272 is engaged with the rotate gear 110, which is secured to the outer tube 28 as described above. Thus, in the rotate position of the shifter mechanism 267, the outer tube 28 rotates about a longitudinal axis of the adapter assembly 20 (FIG. 1) to rotate the end effector 100 about the longitudinal axis of the adapter assembly 20.

FIG. 24 illustrates the shifter mechanism 267 in the articulate position. When the shifter shaft 268 is rotated in the direction of arrow "O" in FIG. 24, the threaded distal portion 268a of the shifter shaft 268 rotates within the threaded bore 130 of the outer housing 24 of the adapter assembly 20 to move the shifter shaft 268 in the direction of arrow "P". As the shifter shaft 268 moves in the direction of arrow "P", the splined extension 272a of the shifter gear 272 is withdrawn from the splined bore 280 of the articulation pinion 270 to disengage the shifter gear 268 from the articulation pinion 270. The articulation pinion 270 is rotatably supported on the shifter shaft 268 and can rotate freely. The shifter gear 272 moves with the shifter shaft 268 and moves into the splined bore 128 of the coupling assembly 22 of the adapter assembly 20. The shifter gear 272 remains engaged with the rotate gear 110 to lock the rotate gear 110 and prevent rotation of the outer tube 28 of the adapter assembly 20. Once the rotate gear 110 is locked, the drive gear 64 (FIG. 3) can be actuated to articulate the end effector 100 as described above with reference to FIG. 20.

FIGS. 25-28 illustrate another alternate version of the shifter mechanism of the adapter assembly of the stapling device shown in FIG. 1 shown generally as shifter mechanism 367 in association with components of the adapter assembly as described above including the outer tube 28, the articulation gear 120, the mounting plate 106, the rotate gear 110, and the body 29' of the coupling assembly 22. The shifter mechanism 367 includes a shifter shaft 368, a splined collar 370, a shifter gear 372, a coupler 374, a first biasing member 378, and a second biasing member 380. The coupler 374 functions in a manner like that of coupler 74 (FIG. 13) and will not be described in further detail herein. The shifter gear 372 is fixedly secured to a central portion of the shifter shaft 368 and rotates with the shifter shaft 368. The distal portion 368a of the shifter shaft 368 is threaded and is received in the threaded bore 130 (FIG. 27) formed in the hollow body 86 of the outer housing 24 (FIG. 27) of the adapter assembly 20. Rotation of the shifter shaft 368 causes longitudinal movement of the shifter shaft 368 within the threaded bore 130.

The splined collar 370 defines a splined bore 382 and includes a pair of outwardly extending wings 384. The body 29' of the coupling assembly 22 defines a bore 386 having slots 388 (FIG. 26) that receive the wings 384 of the splined collar 370 to rotatably fix the splined collar 370 within the splined bore 382. The first biasing member 378 is supported within the body 29' of the coupling assembly 22 and urges the splined collar 370 distally within the bore 386 of the body 29' of the coupling assembly 22. The second biasing member is positioned between the coupler 374 and the shift gear 372 to urge the shift gear 372 distally within the body 29' of the coupling assembly 22.

Figures 27, 28:
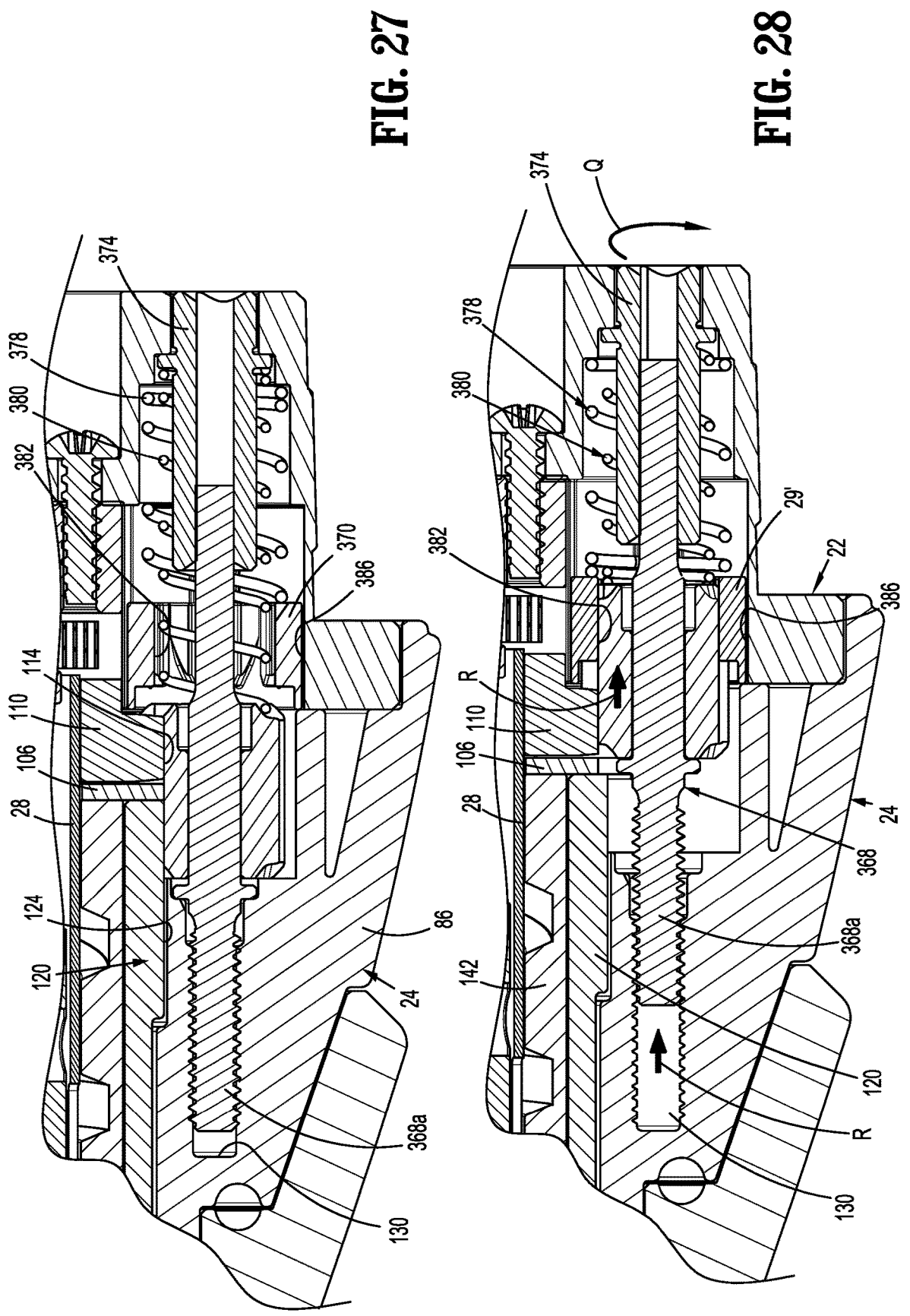
FIG. 27 is a cross-sectional view taken through the adapter assembly including the rotation gear lock shown in FIG. 26 with the adapter assembly in the rotation mode.
FIG. 28 is a cross-sectional view taken through the adapter assembly including the rotation gear lock shown in FIG. 26 as the adapter assembly moves from the rotation mode to the articulation mode.

Like the shifter mechanisms 67 (FIG. 3) and 267 (FIG. 22), the shifter assembly 367 is movable between an articulate position and a rotate position. FIG. 27 illustrates the shifter mechanism 367 in the rotate position. In the rotate position, the shifter gear 372 is engaged with the teeth 124 (FIG. 3) of the articulation gear 120 and the teeth 114 of the rotate gear 110. The shifter gear 372 is positioned distally of the splined collar 370.

As described above (FIG. 3), the gear teeth 124 of the articulation gear 120 are positioned adjacent to the distal face of the mounting plate 106 and are engaged with the drive gear 64 such that rotation of the drive gear 64 rotates the articulation gear 120 within the outer housing 24 of the adapter assembly 20. When the articulation gear 120 rotates, the gear teeth 124 of the articulation gear 120 rotate the spline gear 372 which rotates the rotate gear 110. The rotate gear 110 is secured to the outer tube 28 as described above. Thus, in the rotate position of the shifter mechanism 367, the outer tube 28 rotates with the articulation gear 120 about a longitudinal axis of the adapter assembly 20 (FIG. 1) to rotate the end effector 100 about the longitudinal axis of the adapter assembly 20.

FIG. 28 illustrates the shifter mechanism 367 in the articulate position. When the shifter shaft 368 is rotated in the direction of arrow "Q" in FIG. 28, the threaded distal portion 368a of the shifter shaft 368 rotates within the threaded bore 130 of the outer housing 24 of the adapter assembly 20 (FIG. 1) to move the shifter shaft 368 in the direction of arrow "R". As the shifter shaft 368 moves in the direction of arrow "R", the shifter gear 372 disengages from the articulation gear 120 but remains engaged with the rotate gear 110. As the shifter gear 372 continues to move in the direction of arrow "R", the shifter gear 372 moves into the splined bore 382 of the splined collar 370 but remains engaged with the rotate gear 110 to lock rotation of the rotate gear 110 and prevent rotation of the outer tube 28 of the outer tube 28. Once the rotate gear 110 is locked, the drive gear 64 (FIG. 3) can be actuated to articulate the end effector 100 as described above with reference to FIG. 20.

Persons skilled in the art will understand that the adapter assemblies and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A powered surgical device comprising:

a handle assembly; and an adapter assembly defining a longitudinal axis and including:

a coupling assembly having a body defining a central through bore, a second bore, and a third bore, the body non-rotatably coupled to the handle assembly;

a drive assembly received within the central through bore, the drive assembly including a drive screw and a drive member threadedly coupled to the drive screw, the drive member longitudinally movable along the drive screw in response to rotation of the drive screw;

a drive shaft supporting a drive gear, the drive shaft positioned within the second bore;

an outer tube having a proximal portion and a distal portion, the outer tube rotatable in relation to the coupling assembly;

an articulation mechanism positioned within the outer tube, the articulation mechanism including:

an articulation gear engaged with the drive gear and rotatable in response to rotation of the drive gear;

a barrel cam fixedly supported within the articulation gear, the barrel cam defining first and second cam channels; and a first link extension having a proximal portion and a distal portion, the proximal portion supporting a first cam member that is received in the first cam channel; and a second link extension having a proximal portion and a distal portion, the proximal portion of the second link extension supporting a second cam member that is received in the second cam channel;

a rotate gear coupled to the outer tube and rotatable in relation to the body of the coupling assembly to rotate the outer tube in relation to the coupling assembly; and a shifter mechanism received within the third bore of the body of the coupling assembly and including a shifter shaft and a shifter gear secured to the shifter shaft, the shifter shaft movable between a rotate position in which the shifter gear is coupled with the articulation gear and the rotate gear and an articulate position in which the shifter gear is engaged with the rotate gear and disengaged from the articulation gear.

2. The powered surgical device of claim 1, wherein the body of the coupling assembly of the adapter assembly defines a splined opening, the shifter gear received within the splined opening when the shifter shaft is in the articulate position to prevent rotation of the outer tube in relation to the body of the coupling assembly.

3. The powered surgical device of claim 2, wherein the shifter mechanism includes an articulate pinion that is rotatably supported on the shifter shaft, the articulate pinion defining a splined bore, the shifter gear having a splined extension that is received within the splined bore of the articulate piston to rotatably secure the shifter gear to the articulate piston.

4. The powered surgical device of claim 3, further including a biasing member positioned to urge the splined extension into the splined bore to couple the shifter gear to the articulate pinion.

5. The powered surgical device of claim 2, wherein the shifter mechanism includes a splined collar that is secured within the body of the coupling assembly and defines the splined opening.

6. The powered surgical device of claim 5, wherein the splined collar includes wings, and the body of the coupling assembly defines slots that receive the wings to prevent rotation of the splined collar in relation to the body of the coupling assembly.

7. The powered surgical device of claim 1, further including an end effector supported on the distal portion of the outer tube.

8. The powered surgical device of claim 7, wherein the end effector includes an anvil assembly and a cartridge assembly, the end effector movable between open and clamped positions.

9. The powered surgical device of claim 8, wherein the end effector is secured to the distal portion of the outer tube about an articulation axis that is transverse to the longitudinal axis defined by the adapter assembly.

10. The powered surgical device of claim 9, wherein the first and second link extensions are coupled to the end effector and movable to articulate the end effector about the articulation axis.

11. The powered surgical device of claim 10, wherein the articulation mechanism further includes first and second articulation links, the first articulation link coupling the first link extension to the end effector and the second articulation link coupling the second link extension to the end effector.

12. The powered surgical device of claim 1, wherein the adapter assembly further includes a rotation member supported about the proximal portion of the outer tube, the rotation member being secured to the outer tube by an attachment ring.

13. The powered surgical device of claim 12, wherein the attachment ring includes an annular base and resilient fingers that extend from the annular base, the resilient fingers having inwardly extending tabs, and the outer tube defines spaced openings that receive the tabs.

14. The powered surgical device of claim 1, wherein each of the first and second cam members includes a rectangular body portion, a post, and a follower, the followers received within the first and second cam channels.

15. The powered surgical device of claim 14, wherein that outer tube defines elongate slots, and each of the posts extend through one of the elongate slots such that the first and second link extensions are supported within the outer tube and the followers are positioned on an outer surface of the outer tube.

16. An adapter assembly comprising:

a coupling assembly having a body defining a central through bore, a second bore, and a third bore, the body non-rotatably coupled to the handle assembly;

a rotation member rotatably supported in relation to the body of the coupling assembly;

a drive assembly received within the central through bore, the drive assembly including a drive screw and a drive member threadedly coupled to the drive screw, the drive member longitudinally movable along the drive screw in response to rotation of the drive screw;

a drive shaft supporting a drive gear, the drive shaft positioned within the second bore;

an outer tube having a proximal portion and a distal portion, the outer tube secured to the rotation member and rotatable in relation to the coupling assembly;

an articulation mechanism positioned within the outer tube, the articulation mechanism including:

an articulation gear engaged with the drive gear and rotatable in response to rotation of the drive gear;

a barrel cam fixedly supported within the articulation gear, the barrel cam defining first and second cam channels; and a first link extension having a proximal portion and a distal portion, the proximal portion supporting a first cam member that is received in the first cam channel; and a second link extension having a proximal portion and a distal portion, the proximal portion of the second link extension supporting a second cam member that is received in the second cam channel;

a rotate gear coupled to the outer tube and rotatable in relation to the body of the coupling assembly to rotate the outer tube and the rotation member in relation to the coupling assembly; and a shifter mechanism received within the third bore of the body of the coupling assembly and including a shifter shaft and a shifter gear secured to the shifter shaft, the shifter shaft movable between a rotate position in which the shifter gear is coupled with the articulation gear and the rotate gear and an articulate position in which the shifter gear is engaged with the rotate gear and disengaged from the articulation gear.

17. The adapter assembly of claim 16, wherein the body of the coupling assembly of the adapter assembly defines a splined opening, the shifter gear received within the splined opening when the shifter shaft is in the articulate position to prevent rotation of the outer tube in relation to the body of the coupling assembly.

18. The adapter assembly of claim 17, wherein the shifter mechanism includes an articulate pinion that is rotatably supported on the shifter shaft, the articulate pinion defining a splined bore, the shifter gear having a splined extension that is received within the splined bore of the articulate piston to rotatably secure the shifter gear to the articulate piston.

19. The adapter assembly of claim 17, wherein the shifter mechanism includes a splined collar that is secured within the body of the coupling assembly and defines the splined opening.

20. A powered surgical device comprising:
a handle assembly; and
an adapter assembly defining a longitudinal axis and including:
a coupling assembly having a body defining a central through bore, a second bore, and a third bore, the body non-rotatably coupled to the handle assembly;

a drive assembly received within the central through bore, the drive assembly including a drive screw and a drive member threadedly coupled to the drive screw, the drive member longitudinally movable along the drive screw in response to rotation of the drive screw;

a drive shaft supporting a drive gear, the drive shaft positioned within the second bore;

an outer tube having a proximal portion and a distal portion, the outer tube rotatable in relation to the coupling assembly;

an articulation mechanism positioned within the outer tube, the articulation mechanism including:
an articulation gear engaged with the drive gear and rotatable in response to rotation of the drive gear;
a barrel cam fixedly supported within the articulation gear, the barrel cam defining first and second cam channels; and
a first link extension having a proximal portion and a distal portion, the proximal portion supporting a first cam member that is received in the first cam channel; and
a second link extension having a proximal portion and a distal portion, the proximal portion of the second link extension supporting a second cam member that is received in the second cam channel;

a rotate gear coupled to the outer tube and rotatable in relation to the body of the coupling assembly to rotate the outer tube in relation to the coupling assembly;

a shifter mechanism received within the third bore of the body of the coupling assembly and including a shifter shaft and a shifter gear secured to the shifter shaft, the shifter shaft movable between a rotate position in which the shifter gear is coupled with the articulation gear and the rotate gear and an articulate position in which the shifter gear is engaged with the rotate gear and disengaged from the articulation gear; and an end effector secured to the distal portion of the adapter assembly about an articulation axis that is transverse to the longitudinal axis, the end effector including an anvil assembly and a cartridge assembly, the first and second link extensions coupled to the end effector and movable to articulate the end effector about the articulation axis.

* * * * *